United States Patent
Scott et al.

(10) Patent No.: US 9,689,855 B2
(45) Date of Patent: Jun. 27, 2017

(54) SUBMERSIBLE MULTI-PARAMETER SONDE HAVING A HIGH SENSOR FORM FACTOR SENSOR

(71) Applicant: In-Situ, Inc., Fort Collins, CA (US)

(72) Inventors: Elijah Lyle Scott, Loveland, CO (US); Steven Collin Sewell, Fort Collins, CO (US); Duane B. McKee, Fort Collins, CO (US)

(73) Assignee: In-Situ, Inc., Fort Collins, CO (US)

( * ) Notice: Subject to any disclaimer, the term of this patent is extended or adjusted under 35 U.S.C. 154(b) by 0 days.

(21) Appl. No.: 14/937,138

(22) Filed: Nov. 10, 2015

(65) Prior Publication Data
US 2016/0139101 A1    May 19, 2016

Related U.S. Application Data

(60) Provisional application No. 62/077,528, filed on Nov. 10, 2014, provisional application No. 62/077,627, filed on Nov. 10, 2014, provisional application No. 62/115,466, filed on Feb. 12, 2015, provisional application No. 62/115,593, filed on Feb. 12, 2015.

(51) Int. Cl.
*G01N 33/18* (2006.01)
*G01D 11/24* (2006.01)

(52) U.S. Cl.
CPC ......... *G01N 33/1886* (2013.01); *G01D 11/24* (2013.01); *G01N 33/18* (2013.01)

(58) Field of Classification Search
CPC ..... G01N 33/18; G01N 33/1886; G01D 11/24
See application file for complete search history.

(56) References Cited

U.S. PATENT DOCUMENTS

| | | |
|---|---|---|
| 5,099,920 A | 3/1992 | Warburton et al. |
| 5,259,452 A | 11/1993 | Wittrisch |
| D371,517 S | 7/1996 | Narayanan |

(Continued)

FOREIGN PATENT DOCUMENTS

| | | |
|---|---|---|
| EP | 1851537 | 9/2013 |
| WO | WO 2006/088829 | 8/2006 |
| WO | WO2014125457 | 8/2014 |

OTHER PUBLICATIONS

U.S. Appl. No. 29/558,419, filed Mar. 17, 2016, Scott et al.

(Continued)

*Primary Examiner* — Hezron E Williams
*Assistant Examiner* — David Z Huang
(74) *Attorney, Agent, or Firm* — Lathrop & Gage LLP

(57) ABSTRACT

Provided are multi-parameter sonde systems having a unique form-factor, wherein the plurality of sensors are arranged in a tight-fit configuration. This provides a single distal sensing surface and minimal separation distance between adjacent sensors. The sensors may be pie shaped with an interlocking feature to tightly hold the sensors together, with a sensor guard disposed over the outer surface of the interlocked sensors. Sensor-guards disclosed herein may have an integrated sensor storage and sensor guard configuration, thereby avoiding a need for a separate storage cup and that are configured to minimize unwanted biological growth. Also provided are uniquely shaped individual sensors having interlocking features to hold several sensors together in a sonde.

25 Claims, 17 Drawing Sheets

(56) References Cited

U.S. PATENT DOCUMENTS

| | | | |
|---|---|---|---|
| 5,596,193 A | 1/1997 | Chutjian et al. | |
| 5,820,416 A | 10/1998 | Carmichael | |
| D418,073 S | 12/1999 | Kreutzer et al. | |
| 6,157,029 A | 12/2000 | Chutjian et al. | |
| 6,234,019 B1* | 5/2001 | Caldeira | G01N 9/26 73/32 R |
| 6,305,944 B1 | 10/2001 | Henry et al. | |
| 6,677,861 B1 | 1/2004 | Henry et al. | |
| 6,779,383 B2 | 8/2004 | Lizotte et al. | |
| 6,798,347 B2 | 9/2004 | Henry et al. | |
| 6,928,864 B1 | 8/2005 | Henry et al. | |
| 6,938,506 B2 | 9/2005 | Henry et al. | |
| 6,943,686 B2 | 9/2005 | Allen | |
| 7,007,541 B2 | 3/2006 | Henry et al. | |
| 7,138,926 B2 | 11/2006 | Henry et al. | |
| 7,142,299 B2 | 11/2006 | Tokhtuev et al. | |
| 7,470,917 B1 | 12/2008 | Hoang et al. | |
| D616,314 S | 5/2010 | Akomolede | |
| 7,832,295 B2 | 11/2010 | Rodriguez et al. | |
| 7,900,528 B2 | 3/2011 | Vincent | |
| 8,429,952 B1 | 4/2013 | Bringhurst et al. | |
| 8,488,122 B2 | 7/2013 | Dong et al. | |
| 8,514,066 B2 | 8/2013 | Harmon | |
| 8,542,189 B2 | 9/2013 | Milne et al. | |
| 8,555,482 B2 | 10/2013 | Metzger | |
| 8,664,938 B2 | 3/2014 | Palassis et al. | |
| 8,797,523 B2 | 8/2014 | Clark | |
| D755,655 S | 5/2016 | Scott et al. | |
| 2003/0117623 A1 | 6/2003 | Tokhtuev et al. | |
| 2003/0148637 A1 | 8/2003 | Henry et al. | |
| 2007/0140921 A1 | 6/2007 | Mitchell | |
| 2008/0300821 A1 | 12/2008 | Frank et al. | |
| 2009/0158819 A1 | 6/2009 | Vincent | |
| 2010/0321046 A1 | 12/2010 | Randall et al. | |
| 2011/0005801 A1 | 1/2011 | Olivier et al. | |
| 2011/0023586 A1 | 2/2011 | Leyer et al. | |
| 2011/0273710 A1 | 11/2011 | Dong et al. | |
| 2012/0242993 A1 | 9/2012 | Schick et al. | |
| 2012/0262618 A1 | 10/2012 | Weakly | |
| 2012/0325018 A1* | 12/2012 | Roth, II | G01L 11/06 73/862.41 |
| 2013/0008466 A1 | 1/2013 | Karagoz | |
| 2013/0090789 A1 | 4/2013 | DeDonato | |
| 2014/0017143 A1 | 1/2014 | Clark | |
| 2016/0139046 A1 | 5/2016 | Baltz et al. | |
| 2016/0139070 A1 | 5/2016 | Scott et al. | |
| 2016/0146777 A1 | 5/2016 | McKee | |

OTHER PUBLICATIONS

U.S. Appl. No. 29/558,413, filed Mar. 17, 2016, Scott et al.
U.S. Appl. No. 29/558,414, filed Mar. 17, 2016, Scott et al.
U.S. Appl. No. 29/558,417, filed Mar. 17, 2016, Scott et al.
U.S. Appl. No. 15/148,832, filed May 6, 2016, Steinbach et al.
Sonde Wikipedia, accessed Nov. 4, 2015.
Teledyne Isco AQ700 Water Quality Multi-Parameter Sonde, 2 pages, Sep. 2013.
YSI EXO1 Multiparameter Sonde, http://www.ysi.com/productsdetail.php?EXO1-Water-Quality-Sonde-89, webpage publicly available at least as early as Oct. 2014.
YSI EXO2 Multiparameter Sonde, https://www.ysi.com/EXO2, webpage publicly available at least as early as Oct. 2014.
Hydrolab HL4 http://hydrolab.com/hydrolab-h14-multiparameter-sonde/, webpage publicly available at least as early as May 6, 2014.
Ott Hydrolab DS5 http://www.ott.com/products/water-quality/hydrolab-ds5-multiparameter-data-sonde/, webpage publicly available at least as early as Oct. 2014.
In Situ TROLL 9500 Multiparameter Sonde, https://in-situ.com/products/water-quality-testing-equipment/troll-9500-multiparameter-sonde/, webpage publicly available at least as early as Apr. 1, 2015.
In Situ Aqua TROLL 600 Multiparameter Sonde, https://in-situ.com/products/water-quality-testing-equipment/aqua-troll-600-multiparameter-sonde/, webpage publicly available at least as early as Sep. 14, 2015.
In Situ AquaTROLL 600 Product Information, https://in-situ.com/blog/introducing-the-aqua-troll-600-water-quality-platform-2/, webpage publicly available at least as early as Sep. 21, 2015.
In Situ AquaTROLL 600 Specification Sheet, https://in-situ.com/wp-content/uploads/2015/09/Aqua_TROLL_600_Spec.pdf, webpage publicly available at least as early as Apr. 30, 2016.
In Situ Water Quality Testing Equipment Products, https://in-situ.com/product-category/water-quality-testing-equipment/, webpage publicly available at least as early as Apr. 1, 2015.
Examiner's Report for corresponding CA Application No. 163113, dated Nov. 16, 2015, 3 pages.
6-Series Multiparameter Water Quality Sondes, YSI Environmental, dated Aug. 24, 2006, 14 pages.
International Search Report with Written Opinion corresponding to International Patent Application No. PCT/US2015/059925, mailed Jan. 20, 2016, 8 pages.
International Search Report with Written Opinion corresponding to International Patent Application No. PCT/US2015/059920, mailed Jan. 29, 2016, 7 pages.
International Search Report and Written Opinion corresponding to International Patent Application No. PCT/US2015/059918, mailed Feb. 1, 2016, 8 pages.
International Search Report with Written Opinion corresponding to International Patent Application No. PCT/US2015/059939, mailed Jan. 13, 2016, 9 pages.
International Search Report and the Written Opinion of the International Searching Authority corresponding to International Patent Application No. PCT/US16/31268, dated Aug. 29, 2016.

* cited by examiner

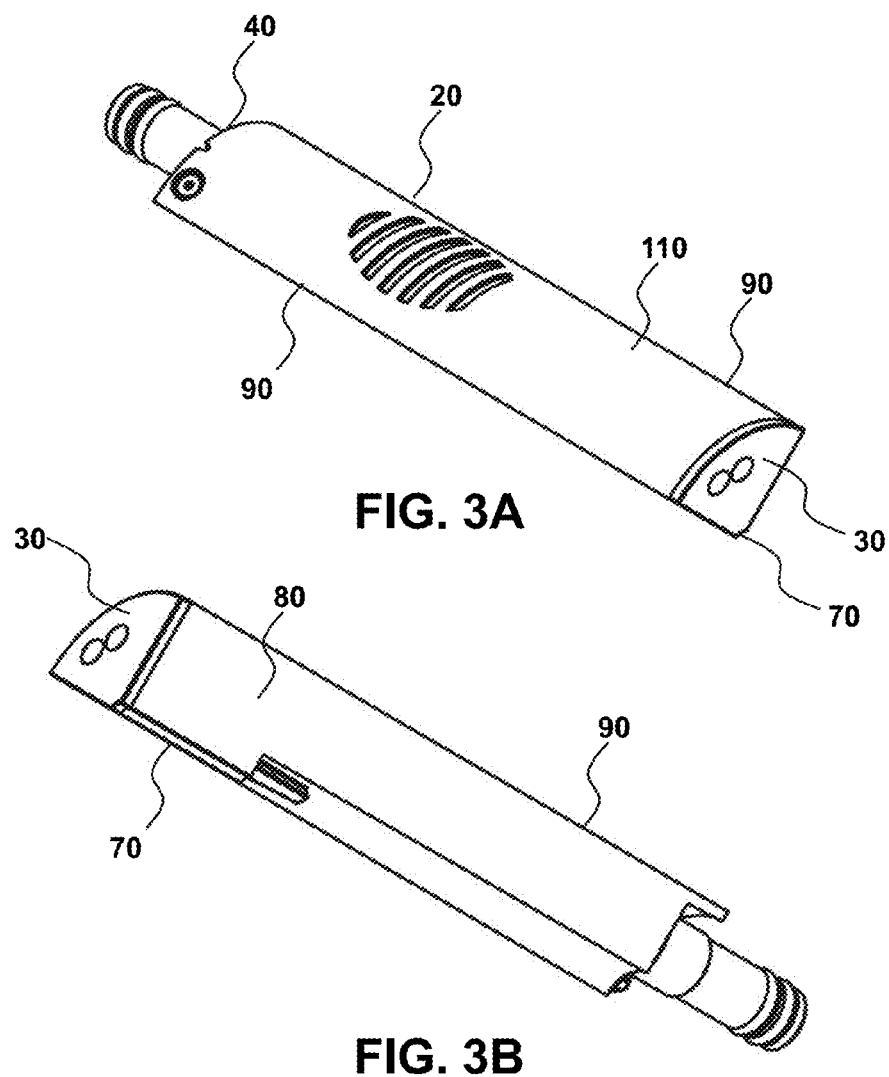
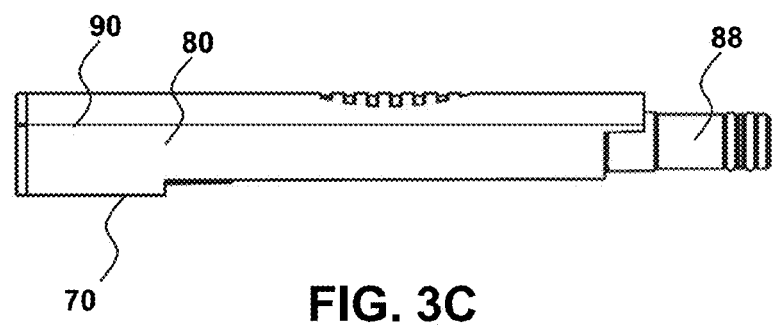

US 9,689,855 B2

SUBMERSIBLE MULTI-PARAMETER SONDE HAVING A HIGH SENSOR FORM FACTOR SENSOR

CROSS-REFERENCE TO RELATED APPLICATIONS

This application claims the benefit of priority of U.S. Provisional Application Ser. Nos. 62/077,528 and 62/077,627 filed Nov. 10, 2014, and 62/115,466 and 62/115,593 filed Feb. 12, 2015, the disclosures of which are each individually incorporated by reference to the extent not inconsistent herewith.

BACKGROUND OF INVENTION

Provided herein are water quality instruments containing multiple sensors for measuring a plurality of water-related parameters. The sensors are uniquely configured to have an extremely high form factor so that they may be contained within a housing that minimizes dead space between sensors and within the housing, with the individual sensor ends forming a single continuous sensing surface. This provides a number of functional benefits in the field of multi-parameter sondes and related sensing methods.

Conventional multi-parameter sondes use a plurality of round or circular sensors that are aligned in a longitudinal direction. With the circular-based geometry, there is substantial dead space or void volume between the sensors, resulting in a number of disadvantages. For example, this dead space must be filled with a fluid in order to ensure appropriate sensor coverage and, therefore, significantly increases the amount of fluid required during sampling. Larger fluid volumes tend to require longer testing times, particularly for low-flow sensing applications, such as sampling from well water. In addition, many sensors require periodic calibration, including prior to data acquisition. This requires a calibration solution and certain calibration solutions are expensive, such as in the $100's/L range.

The large dead space also suffers from the tendency for biological growth to occur in the dead space and on and over the sensors. This is particularly problematic for long deployments, where the large available surface area in long term contact with biologically active water provides a large surface for biological growth, such as from plants, algae and/or animals that anchor to a wetted surface. Multi-parameter sondes with spaced-apart sensors suffer from significant biological growth which must be cleaned to avoid sensor fouling and maintain sensitivity. The open spaces between sensing surfaces makes it difficult to effectively and efficiently automate cleaning, such as with a brush-type wiper.

In view of these limitations, there is a need in the art for fundamentally different sonde configurations and related components that avoid the large open spaces between sensors. Provided herein are sensors with a fundamental change in structure that address the limitations of conventional sonde sensors, and sondes that incorporate the sensors provided herein with additional components that provide fundamental benefits and attendant improved sonde reliability, durability, and sensitivity.

SUMMARY OF THE INVENTION

Conventional multi-parameter sondes generally incorporate round-type sensors that extend from a body. This results in substantial space between sensors that, during use, is filled with a liquid such as a water sample, a calibration fluid, or a storage fluid. Provided herein are sensors that address this limitation by specially shaped sensors that facilitate tight-fit and an attendant tightly packaged multi-sensor configuration. Instead of the uniformly rounded side walls found in conventional sensors, side walls of the instant sensor lie in substantially or entirely a single plane. In this manner, different sensors may tightly contact each other, thereby minimizing and substantially avoiding dead space. Furthermore, the distal end of the sensors, which are adjacent to each other, form a single sensing surface in a generally continuous and flat plane. Accordingly, a composite single sensor surface is formed from a plurality of independent sensors. This aspect may then be leveraged into an improved configuration for a number of other sonde components. For example, a unique interlocking configuration may be employed from a single central support to reliably anchor the sensors in an independent manner without sacrificing the ability to remove and replace individual sensors.

The tightly-fitting plurality of sensors also provides improved ruggedness in that the sensors are more impact resistant compared to the more widely spaced-apart sensors in conventional sondes. The unique outer shape of the combination of sensors in the tight-fit configuration facilitates a tight fit sensor guard that further constrains the sensors and prevents, for example, sensor deflection during an impact event. In contrast, conventional sondes having dead space between sensors, suffer from substantial sensor deflection during an impact event, even for when the sensors are positioned within a guard-type structure.

Provided herein are multi-parameter sondes, and specific components thereof, including sonde sensors, sensor guards having an integrated sensor storage configuration, wipers that prevent unwanted build-up over the sensor and in the volume between the sensor sensing surface and the guard. Also provided are methods of using or making any of the sondes and components herein.

In an embodiment, provided is a multi-parameter sonde comprising a plurality of independent sensors each having a distal sensing surface and a proximal end. In this manner, the sensors may generally be described as longitudinally extending in that the longest dimension is in the longitudinal direction extending between the ends. A base operably connects to the proximal end of each of the sensors. Adjacent distal sensing surfaces contact each other to form a continuous distal sensing surface comprising the plurality of independent sensors. In this manner, substantial gaps or empty spaces between adjacent sensors are avoided.

The base communicates with the sensors, such as by providing commands to and receiving data from the sensors, and contains other relevant electronics such as for displaying information, recording readings, and outputting readings, as well as related components including a power source and connections thereto, including as provided by U.S. Provisional Patent Application by Duane McKee titled "Integrated User Interface for Status and Control of a Submersible Multi-Parameter Sonde" filed Nov. 10, 2014.

Each of the plurality of independent sensors comprise an inner corner edge and a pair of side surfaces extending from the inner corner edge. The sides end at an outer edge and define a plane. The planes are separated from each other by a side angle. An outer facing surface connects the pair of side surfaces at the outer edge, thereby forming a three-sided sensor housing. Accordingly, adjacent sensors may have their sides in intimate contact with each other, with an external surface formed by the plurality of outer-facing surfaces. For example, in use the side surfaces of adjacent sensors are in substantially continuous contact or continuous contact.

The outer surface has any desired shape. For example, if a straight-edge outer surface is desired, the outer surface may comprise a portion that is straight-edged or may be entirely straight-edged (e.g., triangle cross section). In an aspect, the plurality of sensors form an outer surface having circular cross-section. In this manner, each individual sensor has a curved outer surface that forms part of a circle, with a length that extends between the side outer edges defined by the side angle and the length of the side from the inner corner edge, also referred herein as a radial dimension or distance.

The multi-parameter sonde provided herein is compatible with any number of individual sensors. For example, the base may operably connect between 2 and 12 sensors and the side angle may be correspondingly selected such as from a range that is greater than or equal to 30° and less than or equal to 180°.

In one embodiment, the base operably connects four sensors, each sensor having a side angle of 90° and an outer facing surface with a curvature corresponding to one-quarter of a circle so that the plurality of sensors form an outer surface with a cross-section that is substantially circular. Similarly, any number (n) of sensors may be employed, with the resultant external surface formed by the plurality of outer-facing surfaces having a circular cross-section. In this manner, the sum of the n side sensor angles is about 360°.

In many applications, not all the available sensors are required. So that for a sonde having "n" sensors, the application requires a number of sensors less than "n". In such a situation, rather than having an unneeded and expensive sensor in the sonde, a sensor blank may be used, wherein the sensor blank has an external shape that corresponds to an external shape of the sensor being replaced. For example, for a four-sensor configuration, the sonde may have one sensor blank and three sensors, two sensor blanks and two sensors, or three sensor blanks and one sensor. The sensor blank has a surface shape corresponding to the to-be-replaced sensor, with the internal volume devoid of any expensive sensing and electronic circuitry associated with the sensing functionality.

Any of the multi-parameter sondes provided herein may further comprise a sensor-guard having a sensor receiving volume and a sample sensing volume, wherein the plurality of sensors occupy substantially the entire volume of the sensor receiving volume. The sensor receiving volume corresponds to that portion of the sensor guard that extends from the base to the distal sensing surface. In this aspect, "substantially the entire volume" refers to at least 90%, at least 95% or at least 99% of the sensor receiving volume that is physically occupied by the plurality of sensors. Accordingly, the sondes may be described in terms of dead space or void volume within the sensor guard that is less than 10%, less than 5% or less than 1% of the sensor receiving volume portion of the sensor guard. Of course, there is another portion of the sensor guard that has a liquid-containing volume but that is not considered a dead space or void volume because that portion serves an important functional role of allowing the sensor(s) to measure a water parameter. That portion is also referred herein as the sensing volume and may be between about 30 mL and 100 mL. In an aspect, the dead space or void volume is selected from a range that is between about 1% and 10%, or is about 5%, with a corresponding sensor volume between about 99% and 90% of the possible volume, or about 95%.

In an embodiment, to ensure the distal sensing surfaces form a continuous sensing surface a distal insert surface may span between any open gaps at the distal end, such as a cover with openings for the sensor ends.

Any of the multi-parameter sondes may further comprise a central support extending from the base that independently releasably connects each of the plurality of sensors. In this manner, the sensors may reliably connect at a center edge, to ensure sensors are tightly fit against a central axis of the sonde. In this manner, each of the plurality of sensors comprises a corner edge extending from the distal sensing surface and partway toward the proximal end, the corner edge shaped to receive at least a portion of the central support or a drive shaft extending therefrom; a pair of side surfaces that extend from the corner edge and that are separated from each other by a side angle; and an outer facing surface that connects the pair of side surfaces at an outer edge of each of the side surfaces, thereby forming a three-sided sensor housing.

In an aspect, each of the plurality of sensors further comprise: a top portion of each of the pair of side surfaces having a top width; a bottom portion of each of the pair of side surfaces having a bottom width, wherein the bottom width is less than the top width to thereby form a bottom notch and a notch end surface; a tongue connected to the notch end surface and longitudinally extending partway down the notch; a fastening member to fasten the sensor to the base; wherein in combination, the plurality of sensors form: a top sensing volume having with a central orifice for receiving a drive-shaft extending from the central support; and a bottom portion having a central receiving volume for receiving the central support and a drive shaft motor positioned therein; the central support having a plurality of grooves to operably receive the tongues and independently secure each of the sensors to the central portion. In this manner, the unique geometry of each sensor allows for an important functional benefit related to sensor connection, removal and replacement, without sacrificing the tight-fit and high form factor advantages described herein.

The invention is compatible with other fastening means. For example, the central support may support the tongue and a receiving passage positioned in the sensor. Magnetic connections or set screws may be used, so long as they do not interfere with sensor operation. Snap-fit or quick-release connectors may be similarly incorporated in the central support and in inner facing surface of the sensors.

In an aspect, each of the plurality of sensors are tightly held against the central shaft, and a sensor guard is tight-fitted around an outer edge formed by the outer-facing surfaces of the sensors. This provides the functional benefit of the sonde sensors being able to withstand impact force without deflection and associated risk of damage. This benefit is achieved by the high form factor sensors that facilitate tight packing within the guard.

The outer-facing surface of the sensors may be curved so that the plurality of sensors in combination form a circular cross-section. The plurality of sensors may form a continuous outer-facing surface that is in a tight fit with an inner-facing surface of the sensor guard. The multi-parameter sonde may have a sensor side wall in continuous contact with an adjacent sensor side wall, including in a similar tight-fit configuration. In this manner, the sensor guard proximal portion, also referred herein as sensor receiving volume, is substantially entirely filled with the plurality of sensors.

In an aspect, each of the sensors: extend a longitudinal distance that is greater than or equal to 5 cm and less than or equal to 50 cm; have a radial dimension that is greater than or equal to 1 cm and less than or equal to 10 cm; and wherein the plurality of sensors in combination have a void volume that is less than or equal to 10 mL, or less than or equal to 1 mL, or between about 0.5 mL and 5 mL. The separation distance of adjacent surfaces, and corresponding quantification of "tight-fit" may be determined by estimating the surface area available for wet contact between adjacent surfaces and providing fluid to the system until it is filled to the sensor surface (e.g., the void volume). In an aspect where the sensor radial dimension is about 2 cm and sensor length is about 12 cm, there is a total surface area available for water contact associated with the sensor guard and the adjacent sensor surfaces that is about 240 $cm^2$. With an empirically determined void volume that is less than about 5 mL, or less than about 1 mL, an average separation distance may be calculated. The volume that is meant to hold liquid and for sensing by the sensors may be about 45 mL. Accordingly, in an aspect "tight-fit" refers to surfaces that are separated from each other by a distance that is less than 2 mm, less than 1 mm, less than 0.5 mm, or less than 0.2 mm. In an aspect, the gap between the sensors and the sensor guard is less than 0.2 mm. Similarly, a "continuous surface" may correspond to individual surfaces that are separated from adjacent surfaces by a distance that is less than about 2 mm, less than 1 mm, less than 0.5 mm, or less than 0.3 mm. In an aspect, the separation distance or gap between sensors is about 0.25 mm.

In another aspect, the void volume may be functionally described, such as having at least one dimension associated with a sensor that is sufficiently small that biological growth is substantially constrained. In this aspect, the dimension may be the separation distance between adjacent surfaces, such as, for example, less than less than 1 mm, less than 0.5 mm, or less than 0.3 mm. In this context, "substantially constrained" refers to no biological growth is observable to the naked eye between adjacent surfaces after a time period, such as a time period of up to one month, or longer than one month. Alternatively, any observable growth may be defined as minimal in that there is no measurable impact on sensor or sonde performance. A particularly beneficial aspect of the specially configured sensors and sensor guards is that the air-tight seal between the sensors and guard and the deployment of the sonde into the water results in formation of an air pocket in the small volume between the sensor and guard inner surface. Such an air pocket further inhibits the ability for biological growth and corresponding fouling around the sensor. Instead, even after long-term deployment, biological growth is not observable on surfaces corresponding to the air pocket, but instead is confined only to the wetted surface area, such as at the distal-most portion of the sensor, including the distal-most 10%, 5% or 1% or less length.

In an embodiment, the invention further relates to wipers, as the substantially continuous distal sensing surface provides a well-defined surface without substantial empty spaces that may be cleaned effectively with a wiper, such as a wiper connected to a distal end of the drive shaft for rotably brushing each of the distal sensing surfaces.

The multi-parameter sonde may further comprise a sensor guard that connects to the base and surrounds the plurality of sensors in a tight-fit configuration, the sensor guard having a sample sensing volume formed by a distal portion of a sensor guard sidewall, a sensor guard top surface, and the plurality of distal sensing surfaces, wherein the wiper is positioned within the sample sensing volume. In this aspect, the wiper may comprise a central wiper body connected to the drive shaft, the central wiper body having a lower surface that faces the distal sensing surfaces and an upper surface that faces the sensor guard top surface; a first wiper connected to the lower surface for cleaning the plurality of sensing surfaces; and a second wiper connected to the upper surface for cleaning an inward-facing surface of the sensor guard top surface. In this manner, a single wiper system with the double wiper sides simultaneously cleans both the sensors and the sensor guard cap, including by pushing out debris from the sensor guard cap area. In contrast, conventional systems suffer from the disadvantage of having debris that can build up on the top surface of the sensor guard, which can cause reading errors. This can be avoided herein by use of the double wiper configuration. In an aspect, the wiper comprises a brush, such as a pair of brushes.

The unique configuration of the sensors permit positioning of the components required to move the brush, including motor, slip clutch and drive shaft, within volumes formed by the tight-fit connection of the plurality of sensors. For example, the multi-parameter sonde may further comprise a motor and a slip clutch operably positioned in the central support and connected to the drive shaft to provide rotational motion of the drive shaft and the wiper connected thereto. The slip clutch ensures that should the brush be manually moved, there is not damage to delicate components, such as a gearbox, and associated costly repair and down-time.

In an embodiment, the multi-parameter sonde further comprises a position sensor operably connected to the motor to ensure wiper storage at a wiper stored position that does not adversely affect a sensor function. For example, the wiper storage position may be at a position that is 180° from a sensor that is actively measuring a parameter.

Any of the multi-parameter sondes may further comprise a sensor guard that surrounds the plurality of sensors and connects to the base. As discussed, this unique configuration provides a robust, rugged and impact-resistant sonde.

The sensor guard may have a sensing end comprising a fluid opening or a plurality of fluid openings and a covering end that is liquid tight. The sensing end and the covering end may be separated from each other by a central sensor guard portion. A cap configured to connect to both the sensing end and the covering end is connected, as desired, at either the sensing end or the covering end. Similarly, the sensing end and the covering end are each configured to connect to the base to provide either: (1) a sensor guard configuration for the sensing end aligned with the distal sensing surfaces and the covering end connected to the base; or (2) a sensor storage configuration for the covering end aligned with the distal sensing surfaces and the sensing end connected to the base. The sensor guard is configured to reversibly change between the sensor guard configuration and the sensor storage configuration, such as by switching the cap to the other end of the guard and connecting the open-ended portion of the guard to the base. Any of the connections may be by matching threads and the connection made by a screwing motion of the sensor guard into/out of the base and the cap into/out of the sensor guard ends.

The cap may have an internal surface that opposably faces the continuous sensing distal sensing surface and is separated from the continuous sensing distal sensing surface by a sample distance that is greater than or equal to 1 cm and less than or equal to 10 cm.

The multi-parameter sonde may further comprise a rotatable brush that traverses the sample distance for simultaneous cleaning of the continuous sensing distal surface and the cap internal surface. Simultaneous cleaning refers to the rotation of one drive shaft cleans both surfaces.

In another embodiment, provided is a sensor configured for use in a multi-parameter sonde, including any of the multi-parameter sondes described herein. The sensor comprises an inner corner edge with a pair of side surfaces extending from the inner corner edge and ending at an outer edge. The side surfaces define a plane and the planes are separated from each other by a side angle. An outer facing surface connects the pair of side surfaces at the outer edge, thereby forming a three-sided sensor housing. At one end of the sensor housing there is a distal sensing surface, having the active sensing elements that interact with the fluid sample. At the other end there is a proximal end, wherein the pair of side surfaces and the outer-facing surface longitudinally extend between the proximal and the distal sensing surface to form a sensor housing. A sensor is disposed within the sensor housing and having an active sensing end positioned at the distal sensing surface.

Depending on the number of sensors to be supported by the sonde, the side angle is selected from a range that is greater than 30° and less than or equal to 180°. In an embodiment, the plurality of sondes have a side angle sum that corresponds to 360°, thereby ensuring the sensor guard sensor volume is substantially occupied. In an embodiment, all angles may be the same, with four sensors with 90° side angle, six sensor with 60°, etc. Alternatively, the sensors may have different side angles, such as five sensors of 60° and two with 30°, etc., so long as the total of the side angles is 360°.

In an aspect, any of the sensors have a top portion of each of the pair of sides having a top width; a bottom portion of each of the pair of sides having a bottom width, wherein the bottom width is less than the top width to thereby form a bottom notch and a notch end surface between the top portion and the bottom portion; a tongue connected to the notch end surface and longitudinally extending partway down the notch; and a fastening member connected to the proximal end for operably connecting the sensor to a multi-parameter sonde.

The multi-parameter sonde may have a central support having a plurality of grooves for connecting to a plurality of tongues from a plurality of sensors. The plurality of sensors connected to the multi-parameter sonde forms a closed outer surface that is circular in cross-section.

Another embodiment provided herein is a submersible sonde having an integrated storage cap. This sensor guard is unique in that it can be flipped around and used as storage cup. Conventional instruments have a sensor guard and a separate storage cup. Accordingly, this aspect of the invention completely eliminates a separate part and solves a common user issue where the user in the field retrieves their sonde, but forgets the storage cup. Without a storage cup installed, pH probes can dry out which can cause damage to the sensor. With this embodiment, the user does not have to worry about keeping track of and bringing a storage cup because the storage cup is integrated with the instrument.

The submersible sonde may comprise a base portion and a sensor portion having a proximal end connected to the base portion and a distal sensor end for sensing a water parameter. A reversible sensor guard comprises a sensing end comprising a fluid opening; a covering end that is liquid tight, the sensing end and the covering end may be separated from each other by a central sensor guard portion; a cap that connects to either of the sensing end or the covering end; and the sensor guard is reversibly connected to the base to provide: (1) a sensor guard configuration for the sensing end aligned with the distal sensing surfaces and the covering end connected to the base; and (2) a sensor storage configuration for the covering end aligned with the distal sensing surfaces and the sensing end connected to the base. The sensor guard is configured to reversibly change between the sensor guard configuration and the sensor storage configuration.

Also provided is a method of monitoring one or more water parameters, the method comprising the steps of: immersing any of the multi-parameter sondes provided herein with a sensor guard into water, wherein the multi-parameter sonde is in the sensor guard configuration; forming an air-pocket between an outer-facing surface of the sensors and an inner-facing surface of the guard, wherein the air-pocket forms over 90% or greater of a longitudinal distance of the sensors extending from the base, and less than 10% or less of the longitudinal distance from the distal sensing end is wetted; wherein observable biological growth is prevented in the air pocket and is confined to a biological growth area corresponding to the wetted distal sensor end. In this manner, even for long term monitoring, such as on the order of greater than 30 days, biofouling associated with unwanted biological growth is avoided, with minimal unwanted biological growth between the sensor outer surfaces and the guard inner-surface. This provides the functional benefit of both increased sonde longevity without active maintenance and makes maintenance much more convenient and user-friendly, with minimal cleaning.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 3A-3J are various views of an individual sensor that has been removed from the multi-parameter sonde, such as one of the sensors illustrated in FIG. 2B.

FIGS. 6B-6C illustrate a plurality of single fluid openings. Another example is provided in FIGS. 6A and 6D, with each of the openings of FIGS. 6B-6C provided as two separate openings separated by a separation distance.

DETAILED DESCRIPTION OF THE INVENTION

Figure 1A:
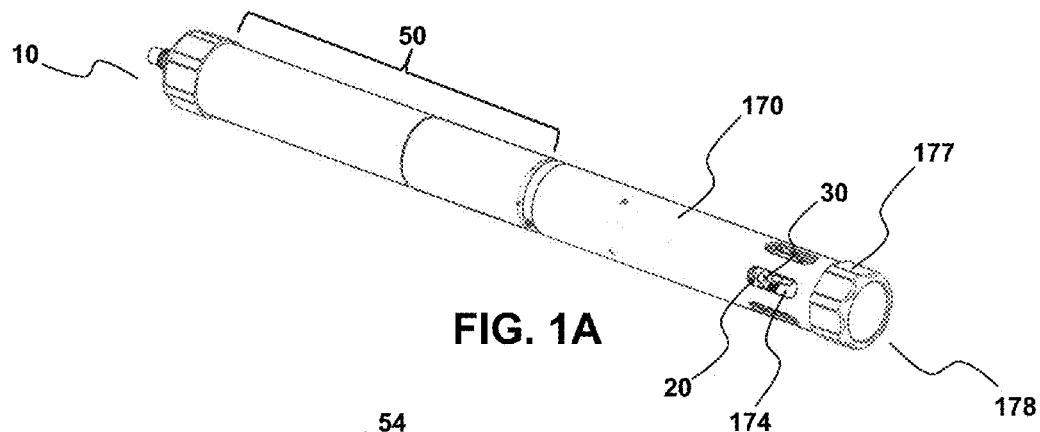
FIG. 1A is a top perspective view of a multi-parameter sonde with a sensor guard in a sensor guard configuration. 1B is a bottom perspective view thereof. 1C is a side view thereof.

In general, the terms and phrases used herein have their art-recognized meaning, which can be found by reference to standard texts, journal references and contexts known to those skilled in the art. The following definitions are provided to clarify their specific use in the context of the invention.

"Sonde" refers to a water quality monitoring instrument. "Multi-parameter" refers to a sonde having multiple independent separate sensors for providing multiple water parameter values.

"Independent sensors" refers to the ability to insert or remove a sensor without affecting other sensors. For example, one of the sensors may be removed and replaced with a sensor blank. Similarly, a user in the field may simply remove one independent sensor and replace it with another of the same or different sensor, without affecting the other sensors. "Sensor blank" refers to an equivalently shaped object that is used in place of a sensor. It is useful if the user does not need or have a sensor to connect to the base so as to fully fill the sensor guard.

The devices provided herein are compatible with a range of sensors, including sensors that measure conductivity, dissolved oxygen (DO), oxygen-reduction potential (ORP), pH, pressure, depth, level, turbidity, ion selective electrodes for various ions, such as nitrate, ammonium and chloride, temperature.

"Continuous distal sensing surface" refers to a plurality of independent sensors that are placed adjacent to each other to form a single surface that, to the naked eye or casual observer, appears continuous. The invention, however, does tolerate some separation distance, preferably less than 2 mm, less than 1 mm, or less than 0.5 mm. Tight-fit and tightly held are used herein in a similar manner, to reflect the minimal space between adjacent surfaces, in contrast to conventional systems that have rather large gaps and attendant large void volumes. Accordingly, adjacent distal sensing surfaces that "substantially contact" each other may refer to an open surface area between sensors that is less than 5%, or less than 1% of the surface area of the continuous distal sensing surface.

Unless defined otherwise, "substantially" refers to a value that is within at least 20%, within at least 10%, or within at least 5% of a desired or true value. Substantially, accordingly, includes a value that matches a desired value.

"Operably connected" refers to a configuration of elements, wherein an action or reaction of one element affects another element, but in a manner that preserves each element's functionality. For example, a wiper operably connected to a center support refers to the ability to move the wiper without impacting the functionality of the center support that supports the sensors in an interlocking configuration.

"Releasably connected" or "releasably connects" refers to a configuration of elements, wherein the elements can be temporarily and reliably connected to each other and, as desired, removed from each other without adversely impacting the functionality of other elements of the device.

"Void volume" refers to the empty space between sensors and between sensors and a side-wall of a cover or a sensor guard. Conventional multi-parameter sondes have void volumes that are relatively large with sufficient separation distances that biological growth can become a significant problem. The low void volumes of the instant devices reflect a tight fit between all adjacent sensors and the side wall of the sensor guard, with separation distances so small that biological growth is substantially constrained. In this aspect, "substantially constrained" refers to minimal growth that does not affect long-term sensor performance. For example, there may be biological growth not observable to the naked eye, or the observable growth is so minor that there is no detectable drop-off in a sensor performance. Void volume may be expressed in terms of a fraction or percentage of guard's sensor receiving volume.

In contrast, "sample volume" or "sensor volume" refers to that part of the system in which fluid is desirably located, such as for water parameter measure or sensor storage. In an aspect, this volume is between about 20 mL and 100 mL, or about 40 mL to 50 mL, depending on sensor size, for example. In comparison, conventional sondes may have up to around double, triple or an order of magnitude volumes, as a result of the substantially large void volume that requires filling so as to ensure the distal sensing surfaces are covered with liquid.

EXAMPLE 1

Multi-Parameter Sonde

A multi-parameter sonde may have pie shaped sensors that fill the entire sensor space of the multi-parameter sonde. Other sondes, in contrast, use mostly round sensors that have open space between sensors.

The pie shape reduces the volume of liquid that surrounds the sensor which has a certain advantages. First, a small volume of water in a flow cell leads to faster testing results during low flow sampling, such as from well water. Second, less calibration solution is required to calibrate and instrument, which can save significant amount of money as some calibration fluids cost several hundred dollars a liter.

In addition, pie shaped sensors are easier to clean after long deployments because the sensors are in direct contact with each other, which reduces the surface area in direct contact with biologically active water that grow algae and other biological growth. Other multi-parameter sondes have sensors that are spread out and the biological growth has to be cleaned in between sensors. The sondes provided herein do not require cleaning in between sensors, even after extended periods of use, such as on the order of weeks or months.

Figure 1B:
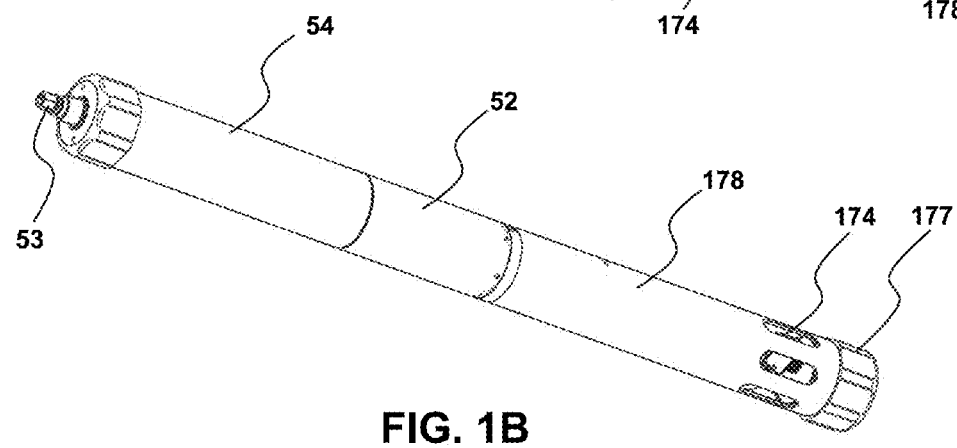
Figure 1C:
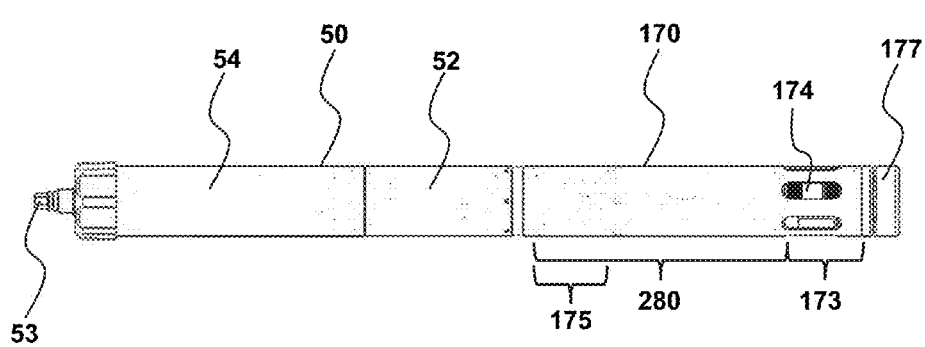

Referring to FIG. 1A-1C, in a fully assembled configuration ready for sensing in a submerged environment, the multi-parameter sonde 10 has a plurality of independent sensors 20 disposed within a sensor guard 170. The sonde is shown in a sensor guard configuration 178 in that the sensing end 173 having a plurality of fluid openings 174 is aligned with the distal sensing surfaces 30 of sensors 20. Covering end 175 is positioned in a proximal position, relative to the sensing end 173 of the sensor guard. The sensing end corresponds to the sample volume. The sensor guard is open-ended, with one end, the proximal end, closed via the connection with the base 50 and the other end, the distal end, closed via the cap 177. Sensor receiving volume 280 corresponds to the portion of the sensor guard 170 in which the sensors extend and, therefore, depends on the sensor longitudinal length. The volume of sensing volume 173 may be about 40 mL-50 mL, or about 46 mL.

The base 50 may further comprise a display portion 52 for indicating sonde and sensor status, and a base end 54 for containing other sonde components, such as power supply, electronics and external connection port 53.

Figure 2A:
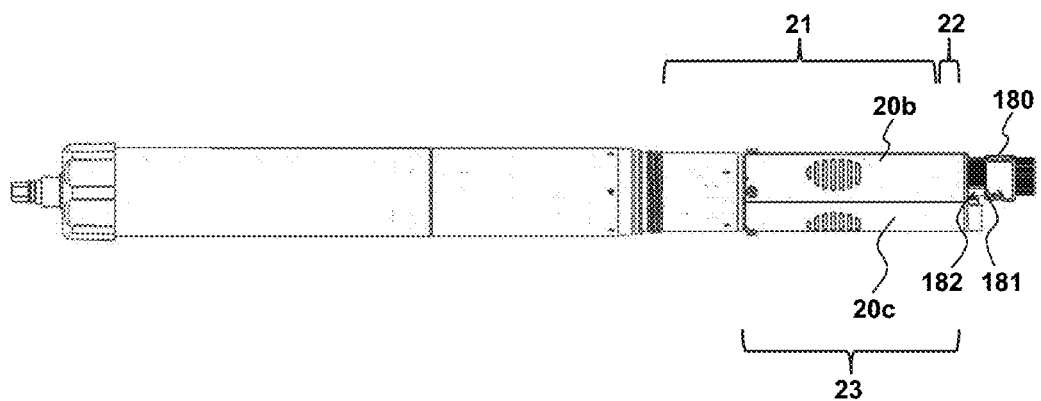
FIG. 2A is a side view of the multi-parameter sonde of 1A with the sensor guard removed to show the plurality of sensors that are in an adjacent configuration and a cleaning brush that are normally confined within a sensor guard during use. 2B is a perspective view thereof.
Figure 2B:
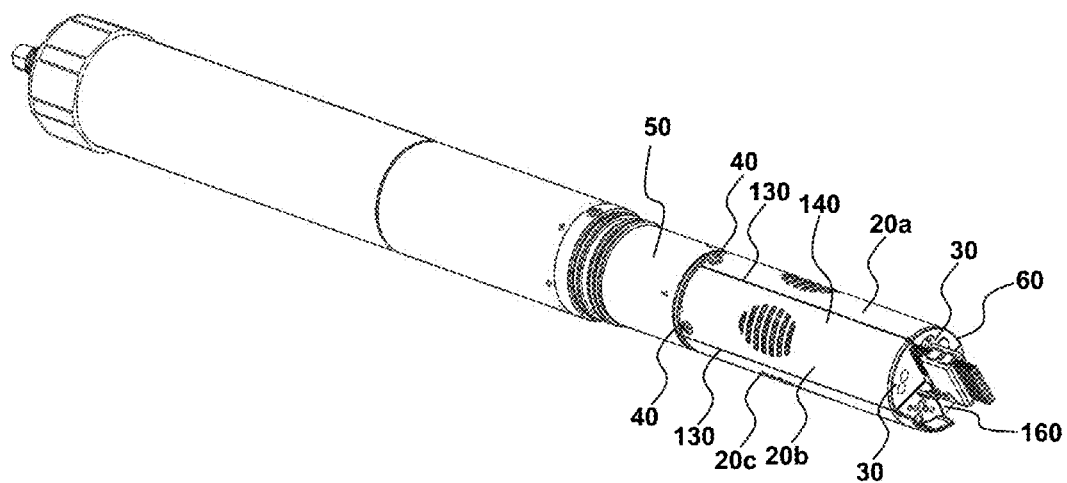

A multi-parameter sonde with the sensor guard 170 removed is illustrated in FIG. 2A-2B. Plurality of independent sensors 20 (20a 20b 20c 20d) (shown as sensor blank 160)) each have a distal sensing surface 30 and a proximal end 40 connected to the base 50. As shown in FIG. 2B, adjacent distal sensing surfaces contact each other to form a continuous distal sensing surface 60 having a substantially planar surface. The fitting between the independent sensors is so tight, that the outer surface cross-section visually appears as a solid circle. Because the fit between all the adjacent sensors is close or tight, the sensors are also referred herein as having a high "form factor", with minimal void volume or dead space between the sensors that extend from the base 50 and proximal end 40 to the distal sensing surface 30 and, in combination, the continuous distal sensing surface 60, as discussed further in Example 2. Also illustrated is a wiper 180 that is connected to a distal end 181 of a drive shaft 182. Various dimensions are illustrated with element numbers 21 22 23, with respect to air-pocket formation during use. When sensor guard 170 is in place and the sonde is inserted into liquid water, with distal sensing surface or end 30 in a downward orientation, an air pocket forms between the outer sensor 20 surfaces and a corresponding inner facing sensor guard surface. The air pocket may correspond to the longitudinal dimension 21, where no biological growth is observable, with a wetted surface corresponding to 22, where biological growth may occur, given that wetted region is in water contact. The wetted to non-wetted area or length, may be expressed as a ratio of dimension 22 to 21 (optionally plus 22) or 22 to 23. That ratio may be less than 10%, less than 5% or less than 1%. A wetted region that is confined to within at least 5% of a sensor longitudinal length from the distal sensing surface, accordingly, can correspond generally to dimension 22 divided by dimension 23. In this context "observable" may refer to whether or not biological growth is seen by the naked eye. This reflects that any growth that is not pronounced and observable to the user, such as microscopic-scale growth, will have minimal to no impact on the sensor operation and, therefore, on the cleanability during maintenance.

EXAMPLE 2

High Form Factor Sensor

The sensors may generally be described as "pie shaped", and can have an interlocking feature that holds the sensors together. The interlocking feature can be a tongue and grove design that holds all the sensors to the center support that is operably connected to the wiper. This has a number of benefits, including enhancing impact resistance as the interlocking protects the sensors during a drop or impact in situations where the sensor guard is not installed. It also holds the sensors tightly together and makes sensor guard installation easier. Without the interlocking feature the sensors tend to splay out and have to be pushed together to install the tightly fitting sensor guard.

Figure 3D:
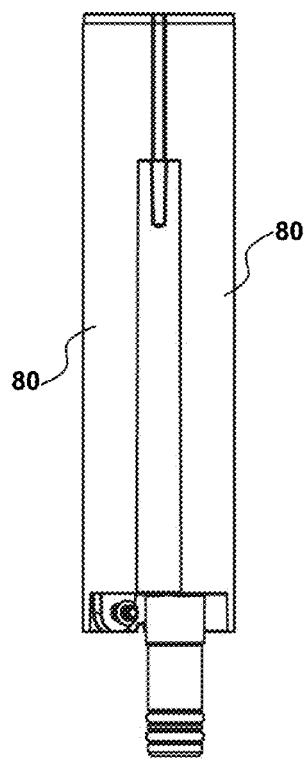
Figure 3E:
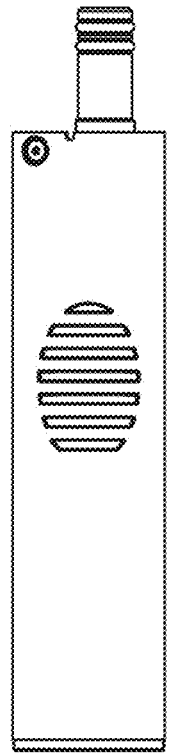
Figure 3F:
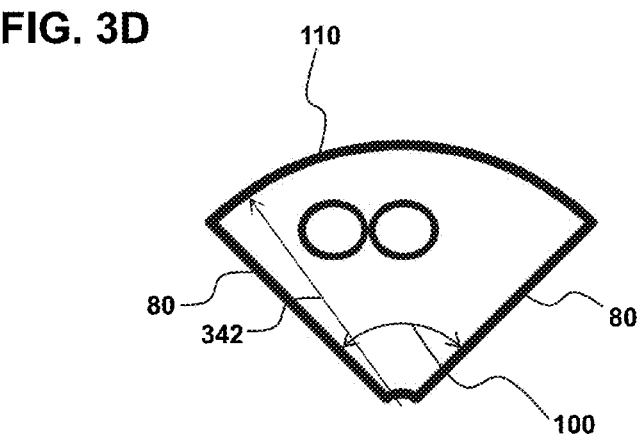
Figure 3G:
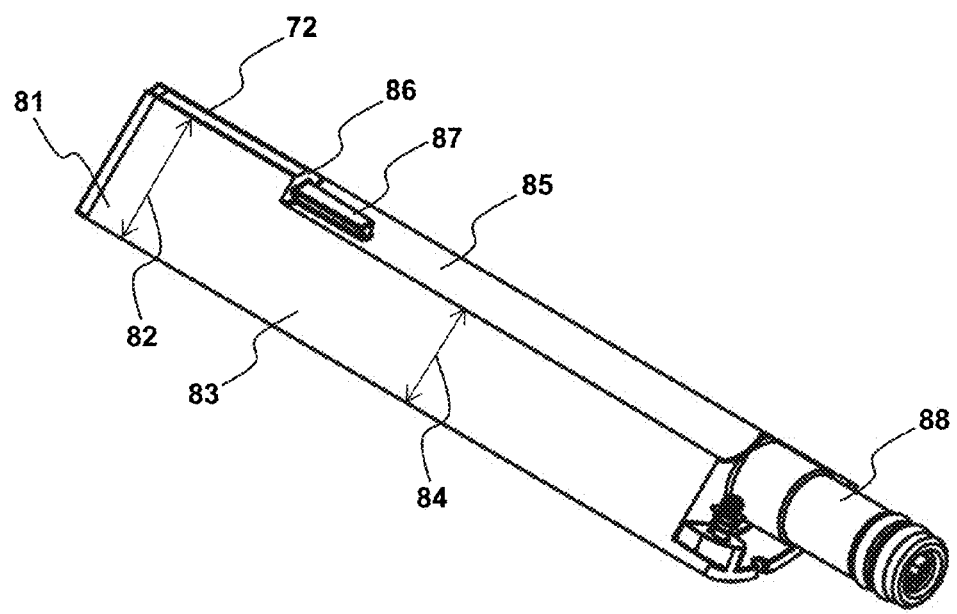
Figure 3H:
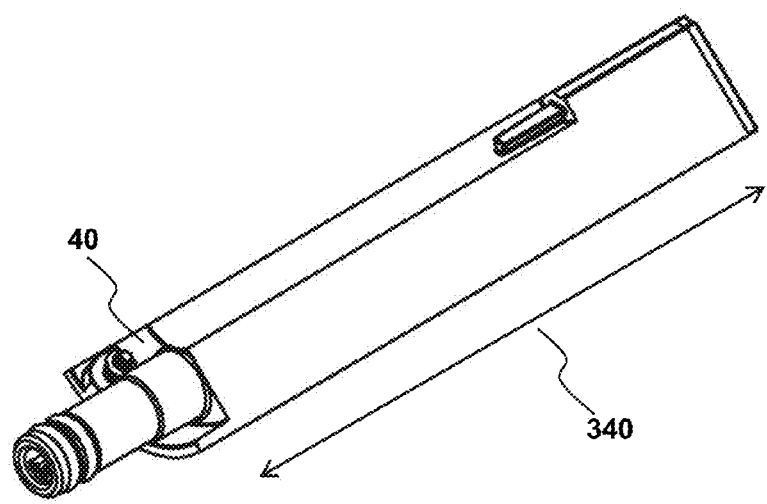
Figure 3I:
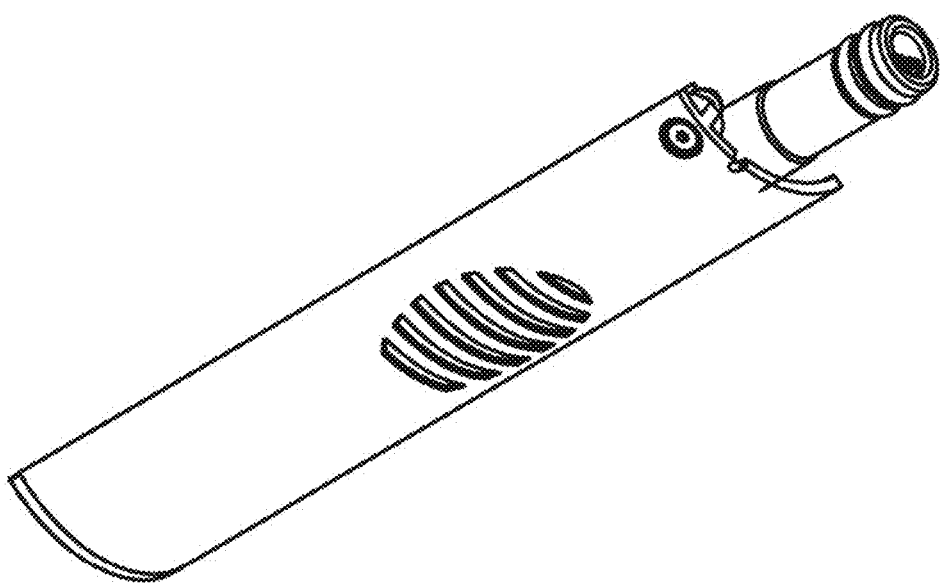
Figure 3J:
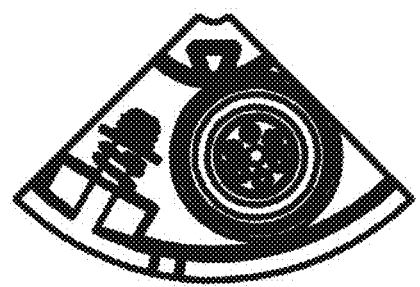

FIGS. 3A-3J are various views of an independent sensor 20. Depending on the sensor type, and more specifically the liquid parameter being measured, the sensor surface 30 will have different sensing elements. There is, however, other common aspects, to the sensors. For example, a corner edge 70, also referred herein as an inner corner edge 70, defines an inward facing orientation of the sensor relative to the sonde center axis. A pair of side surfaces 80 extend from corner edge 70 and end at outer edge 90. The pair of side surfaces 80 are separated from each other by side angle 100 defined as the angle between the planes formed by side surfaces 80 (see, e.g., FIG. 3F). Outer-facing surface 110 extends between the outer edges 90 of the side surface 80, thereby forming a three-sided housing for the sensor, as illustrated in FIGS. 3F and 3J.

For aspects where the distal sensor surfaces have excess space between adjacent edges, a distal insert surface or spacer may be provided to traverse the excess space, thereby functionally providing a continuous distal sensing surface.

The sensors may be provided with an interlocking mechanism. Referring specifically to FIG. 3G, the sensor may have a top portion 81 with a top width 82 and a bottom portion 83 with a bottom width 84. The bottom width 84 is less than the top width 82, thereby forming a bottom notch 85 and notch end surface 86. A tongue 87 extends from the notch end surface 86 in longitudinal direction that aligns with the sensor housing. Fastening member 88 in the sensor proximal end may be used to fasten the sensor to the base, including to provide an electrical connection to the base.

Figure 9:
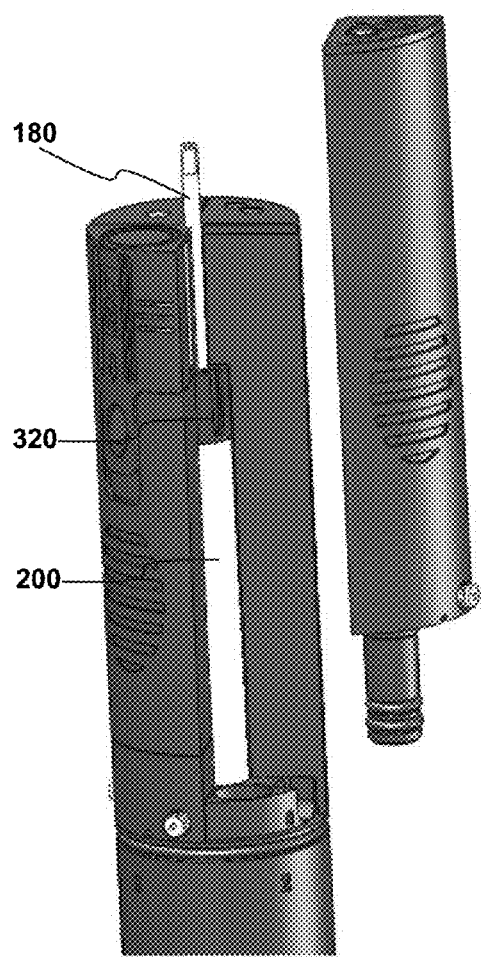
FIG. 9 illustrates the independent removal of one of four sensors from the multi-parameter sonde of FIG. 8, with a corresponding central support member that removably connects each of the sensors.
Figure 10:
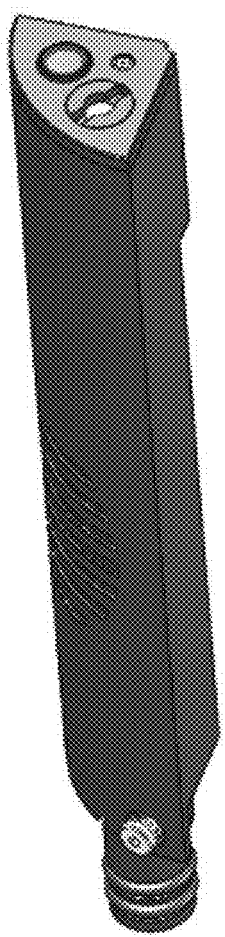
FIG. 10 illustrates one of the sensors from the multi-parameter sonde of FIG. 8 in a removed configuration.
Figure 11:
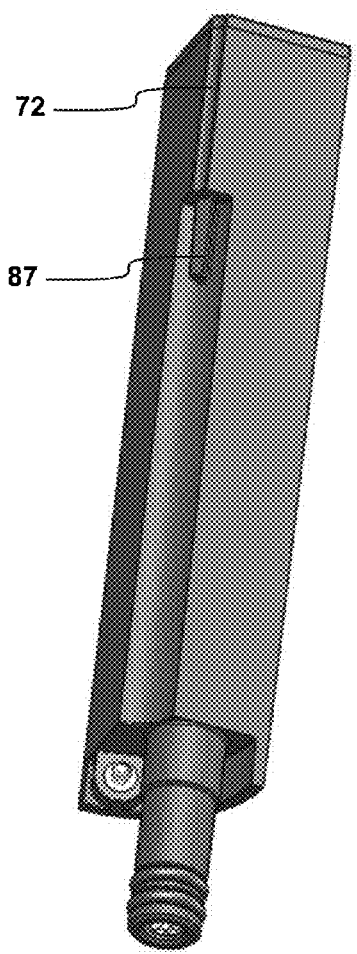
FIG. 11 is a schematic illustration illustrating the inner corner edge of a removed sonde of FIG. 10.

Referring also to FIGS. 8-11, sensors with corner groove 72 of each sensor in a combination of sensors form a central orifice 300 in which drive shaft 182 extends therethrough. The drive shaft rotates wiper 180 which is connected thereto. For additional clarity, FIG. 9 illustrates one of the sensors removed to reveal drive shaft 180 and central support 200, which are not fully visible in the sensor assembled configuration of FIG. 8. Because central support 200 has a larger width than the drive shaft 180, the bottom portion of the sensor has a larger cut-out than the top portion groove. The central support has a plurality of grooves 320 configured to receive from each sensor tongue 87, thereby providing tight contact with the sensors to facilitate placement of sensor guard over the sensors' outer-facing surfaces. Longitudinal direction, unless indicated specifically otherwise, is reflected by arrow 11 in FIG. 8.

The independent sensors may be further defined in terms of a longitudinal distance 340 (FIG. 3H) and a radial dimension 342 (FIG. 3F).

Figure 18:
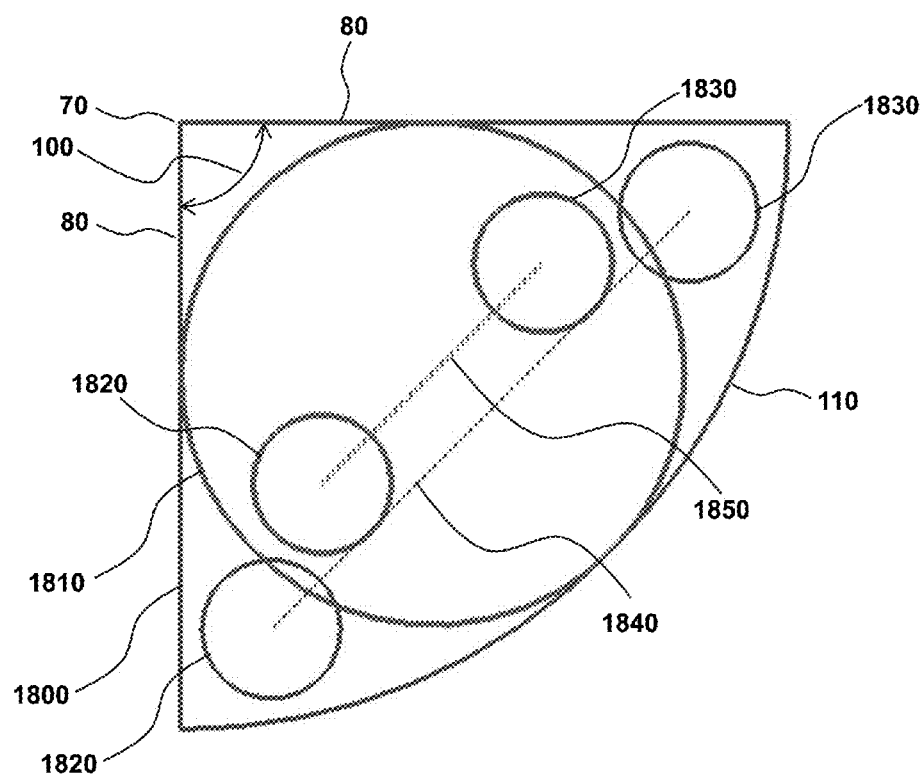
FIG. 18. Schematic illustration comparing the increased distal sensor surface area available to a pie-shaped sensor compared to an equivalent circle-shaped sensor.

The high-form factor sensors may also be described as pie-shaped, referring to a shape of the sensor cross-section having a corner with two-sides, and a curved outer surface. FIG. 18 shows an embodiment where the side angle 100 at corner edge 70 (for clarity, corner groove 72 is not illustrated) that defines the angle between sides 80 of a sensors are 90°, so that four sensors are used in the sonde to provide a cylindrically-shaped high form factor sensor package. This pie-shape, formed by side walls 80 and outer wall 110, besides having benefit of being able to be tightly packed, also provides increased sensitivity, such as for optical-based sensors. A pie shaped sensor 1800 has an increased surface area of 45% compared to an equivalently sized circular shaped sensor 1810, as indicated in FIG. 18. This permits optical spacing increase between emitting 1820 and receiving 1830 optics to be increased in the pie sensor by about 89% (compare separation distance 1840 with 1850) compared to conventional circular-shaped sensors, with attendant increase in sensitivity.

EXAMPLE 3

Sensor Base

Figure 4A:
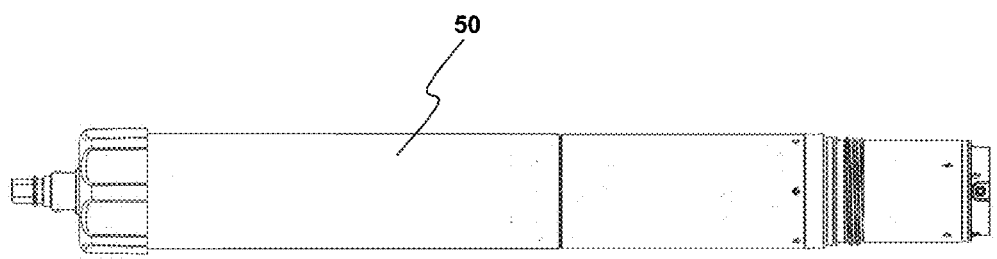
FIG. 4A-4B are illustrations of a base of the multi-parameter sonde, with the sensor guard, plurality of sensors, and central drive shaft removed, from a side and perspective view, respectively.
Figure 4B:
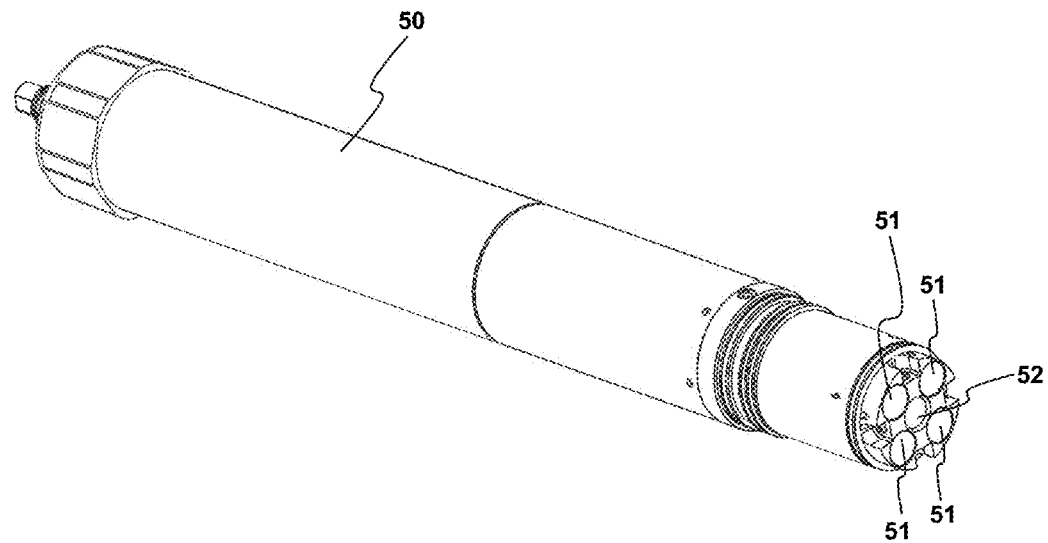

Referring to FIGS. 4A-4B, the sensor base 50 is shown without the sensor guard, the sensors, or the central support. Sensor ports 51 are configured to receive a proximal portion of the sensors, including a fastening member 88 shown in FIG. 3G. In the illustrated embodiment, four ports are shown for receiving four independent sensors, or a combination of sensors and sensor blanks having the same shape of the sensor. The blank sensor is useful for embodiments where not all sensors are needed and that, instead of occupying the space with an unused sensor, a relatively cheap blank may be used so as to maintain the many advantages described herein. Central support port 52 may be used to operably connect central support and attendant drive shaft extending therefrom. The port connections provide a reliable connection in a manner that also ensures convenient removability. Sensor base may contain other components for sonde functionality, operability and control, including such as by connector 53 for connection to an external electronic device.

EXAMPLE 4

Reversible Sensor Guard

Figure 5A:
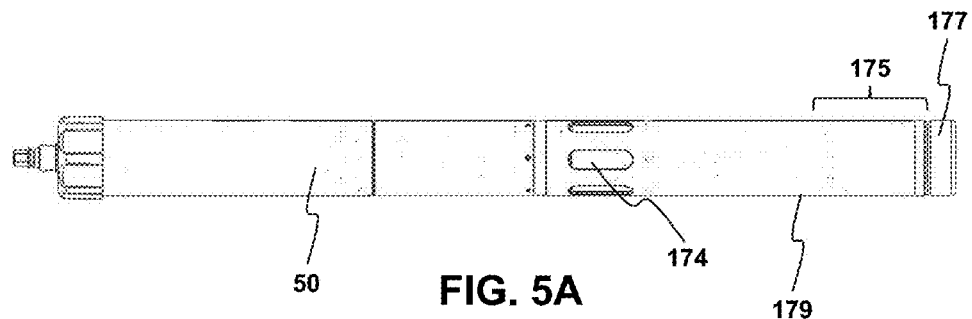
FIG. 5A-5B show the multi-parameter sonde in a sensor storage configuration. 5C is a sectional view of the distal sensing surface and cap, illustrating the sensing volume and sensing separation distance between sensing surface and sensor guard cap inner-facing surface.
Figure 5B:
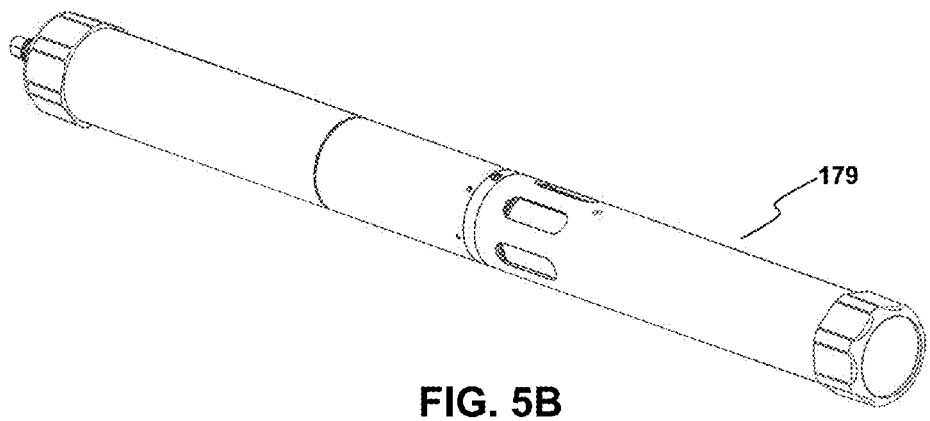

The reversible sensor guard 170 is shown in FIG. 1A-1C in a sensor guard configuration 178 and in FIG. 5A-5B in a sensor storage configuration 179. These different configurations reflect a unique aspect of the instant sondes, namely that the storage cup is an integral part of the system. This avoids the risk of a user forgetting a storage cup in the field, with an attendant risk of permanent sensor damage associated with sensor drying. In the stored configuration 179, the openings 174 are proximally positioned adjacent to the base 50 (FIG. 5A). In contrast, in a sensor guard configuration 178, the passages 174 are positioned distally and adjacent to the sensing surface to facilitate fluid introduction to the sensor surface while still protecting the sensors from unwanted physical contact (FIG. 1A-1C).

Figure 5C:
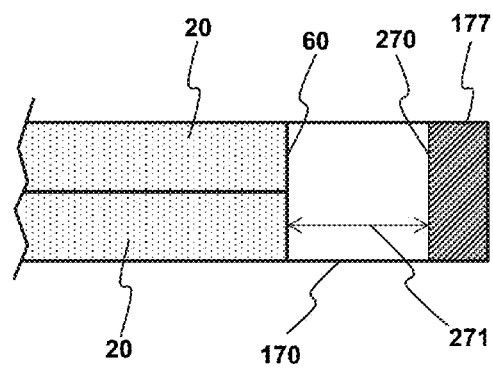

FIG. 5C is a sectional view along a central plane of the distal end of the sensors 20 to the sensor guard cap 177 of sensor guard 170. An internal surface 270 of sensor guard cap 177 faces the distal sensing surface 60, and is separated by a sample distance 271. In the storage configuration 179 of FIGS. 5A-5B, the sample distance forms a storage volume for receiving a liquid to ensure sensors 20 remain wetted to avoid sensor damage, such as during when the sonde is removed from a liquid environment. Accordingly, storage volume is configured to be liquid tight with respect to the surrounding environment. In contrast, for a sensor guard configuration 178 (illustrated in FIG. 1A-1C), the sample distance 271 forms a corresponding sensing volume, but that is, of course, not liquid-tight to the surrounding environment, such as due to the presence of fluid opening(s) 174. In this manner, a single component can serve two different functions depending on orientation: (1) sensor protection during liquid sensing; and (2) sensor storage with a liquid that is maintained in liquid contact with the distal surface 60. This avoids the need, as required in conventional sondes, of carrying a separate cap element. This all-in-one integrated approach is illustrated further in FIG. 14.

Figure 14:
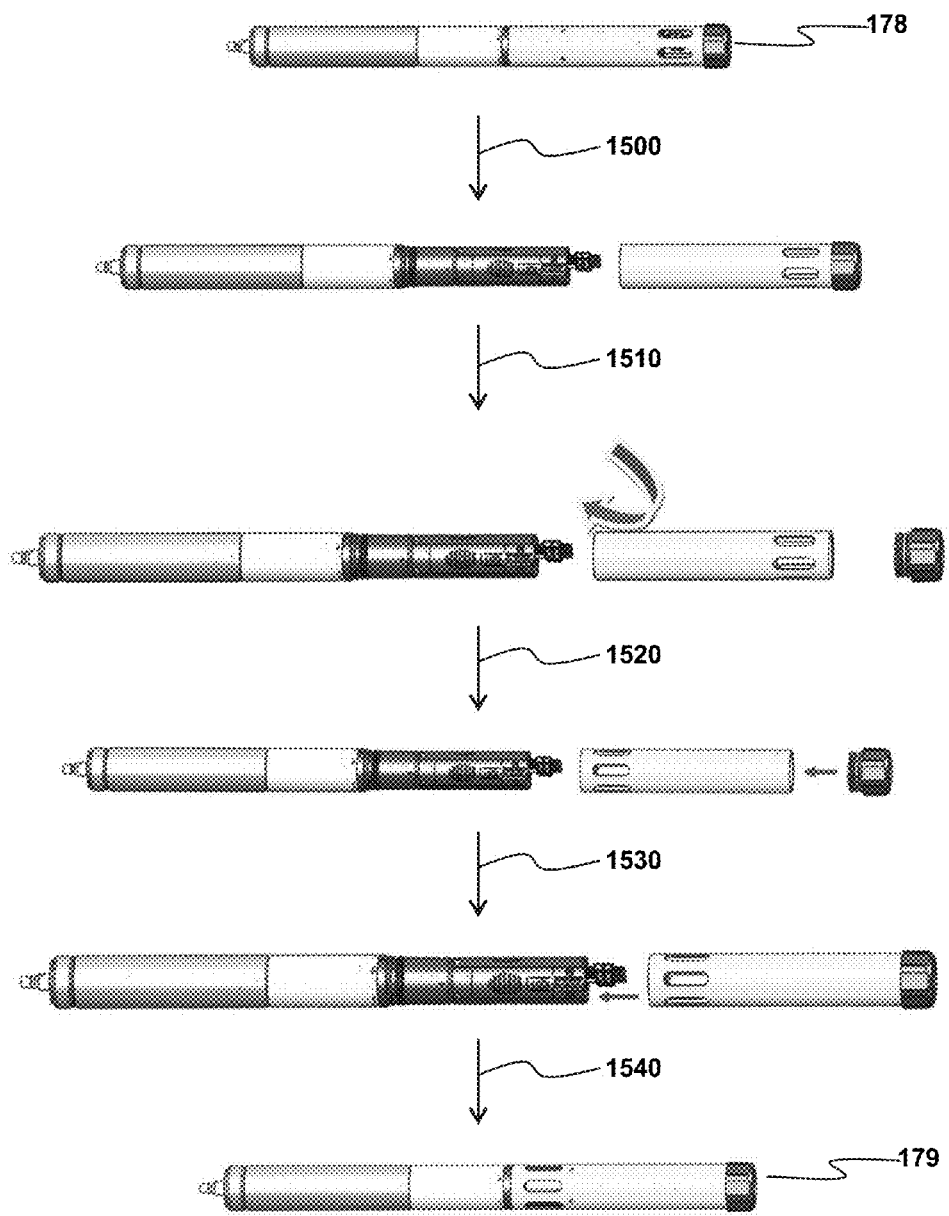
FIG. 14 is a visual process flow summary summarizing the steps for changing a sensor guard from a sensor-guard configuration (top panel) to a sensor-storage position (bottom panel).

FIG. 14 summarizes the steps used to switch between a sensor guard configuration 178 (top panel) and a stored configuration 179 (bottom panel). In step 1500 the sensor guard is removed from the base. The cap is removed from the sensor guard in step 1510. The sensor guard is rotated 1520 so as to move the plurality of fluid openings from a distal position to a proximal position. In step 1530 the cap is reinstalled (now at the other end of the sensor guard). The sensor guard is attached to the base in 1540.

Figure 15:
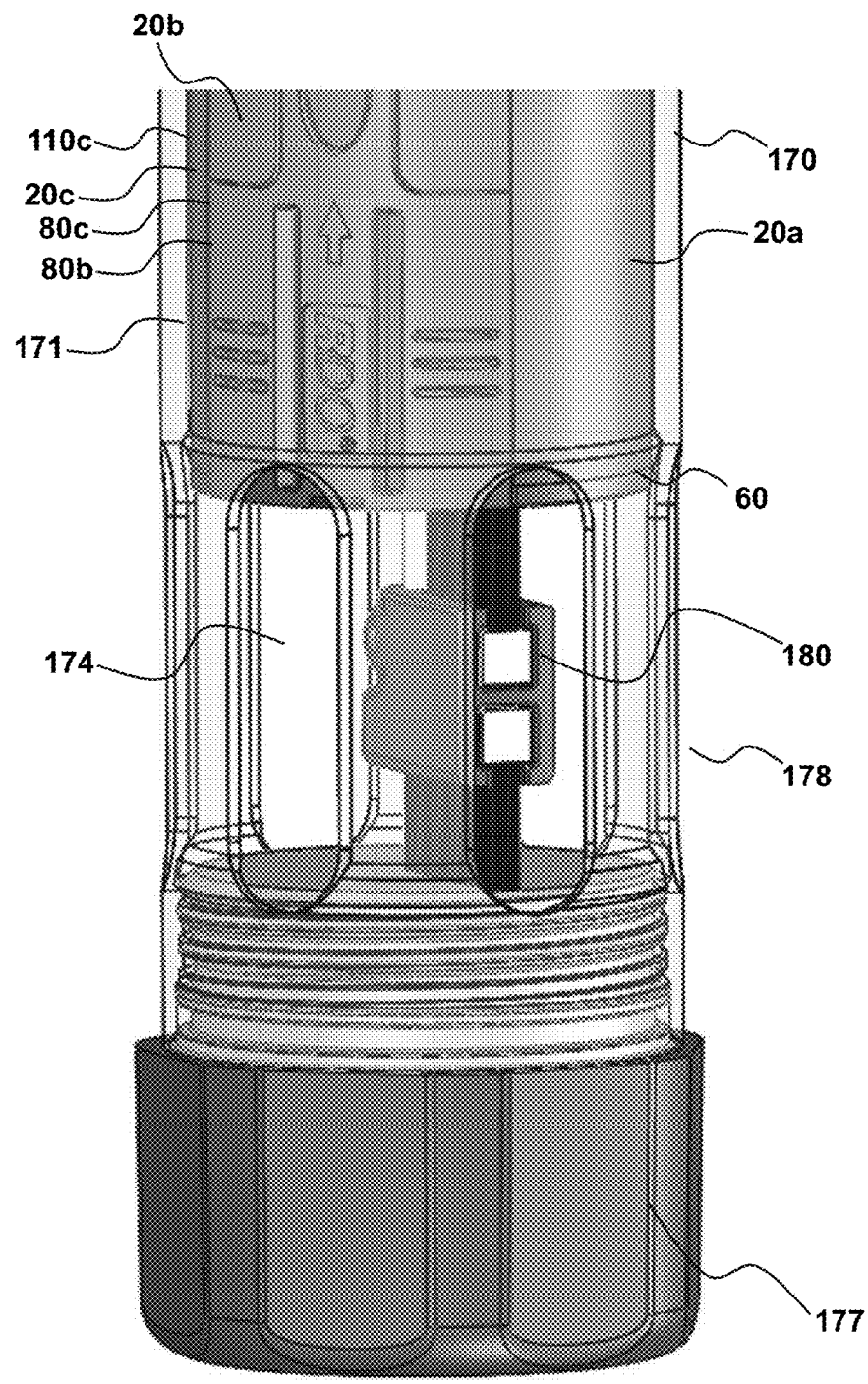
FIG. 15 is a close-up view of the distal sensing surface and sensing volume with sensor guard and wiper.

A close-up view of the sensor guard 170 provided in sensor guard configuration 178 is illustrated in FIG. 15. Also shown is the distal sensing surface 60 formed from the sensors, including the visible sensors 20a 20b 20c, wiper 180, cap 177 and passage 174. FIG. 15 also illustrates the various tight fits such as between sensor guard 170 inner facing surface 171 and sensor 20c outer surface 110c. Also, there is a tight fit between adjacent sensor side walls, with adjacent sensors 20b and 20c having side walls 80b and 80c, having a tight-fit. Although the tight-fit is so close that there is no readily observable gap, the tight-fit need not be liquid-tight. Some liquid is expected to leak between sensors, such as less than 10 mL, or less than about 1 mL. However, the separation distance between adjacent sensors and the outer sensor surface is so small, such as less than 1 mm or 0.5 mm, that there is minimal void volume and biological growth therein is substantially constrained and avoided. The cap may be threaded so as to mate with corresponding threads on either end of the sensor guard 170.

Figure 6A:
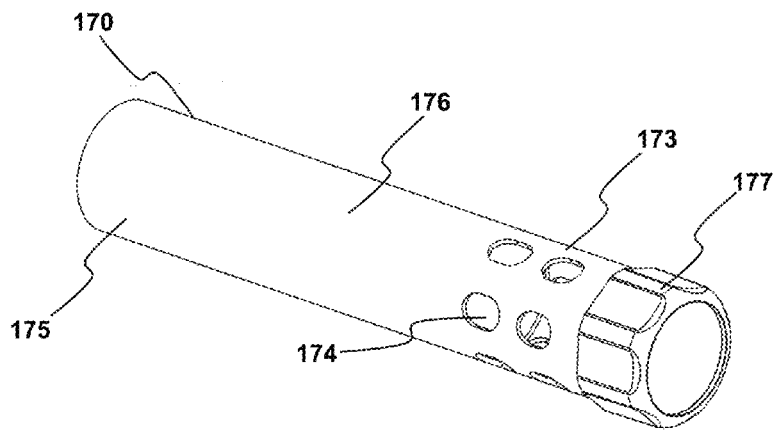
FIG. 6A-6D are illustrations of the sensor guard.
Figure 6C:
Figure 6B:
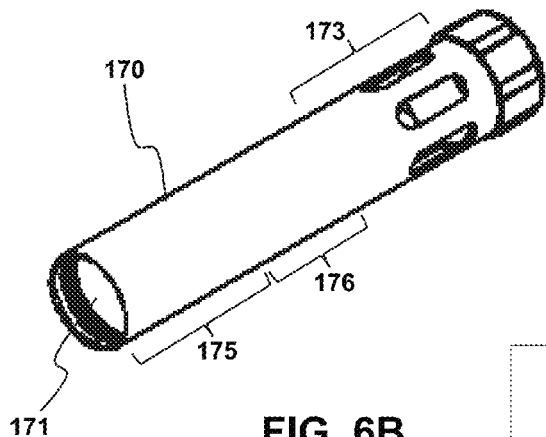
Figure 6D:
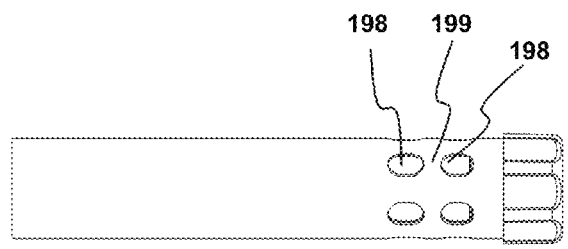

FIGS. 6A-6D, for additional clarity, illustrate a sensor guard removed from the sonde. FIGS. 6B-6C illustrate a plurality of individual passages 174, whereas FIGS. 6A and 6D illustrates each of the individual passages comprising a plurality of passages, in this example two paired passages 198 separated by a separation distance 199. In other words, each of the passages or openings 174 illustrated in FIG. 6B can be split into multiple passages, such as the two passages 198 of FIG. 6D. Use of passages comprising a plurality, such as two individual paired passages separated by a separation distance, can provide improved light characteristics for sensors that provide an output signal based on a light characteristic. The configuration depicted in FIGS. 6A and 6D ensures that irrespective of a light direction or guard orientation, a background light intensity is relatively constant, thereby improving sensor sensitivity, as further explained in U.S. Pat. App. 62/115,593.

EXAMPLE 5

Wipers

The instant single continuous sensing surface allows a sensor cleaning brush to wipe on a flat even surface, without open spaces between sensors. The brushes and wipers are more effective at cleaning because there is not deflection around the sensors due to the space between probes, as is currently found with conventional multi-parameter sondes on the market.

Figure 7A:
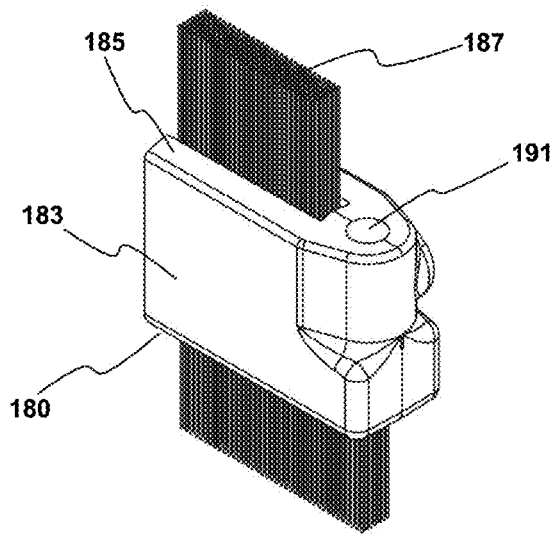
FIG. 7A-7D are illustrations of a wiper that may be connected to the multi-parameter sonde for cleaning to improve sensor reliability and increase sensor longevity.
Figure 7B:
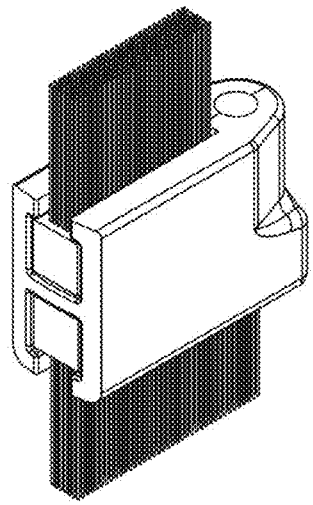
Figure 7C:
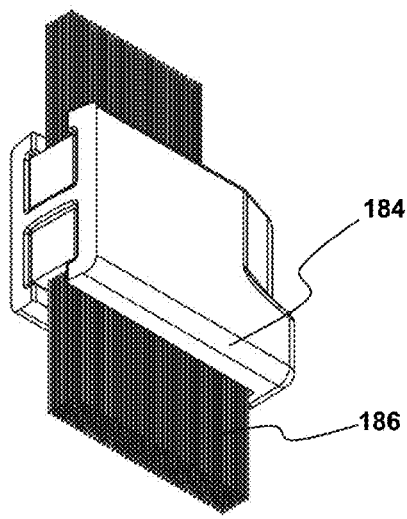
Figure 7D:
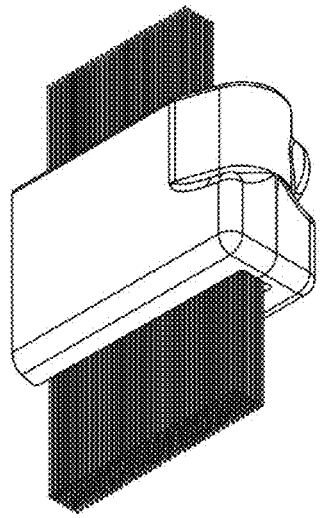
Figure 8:
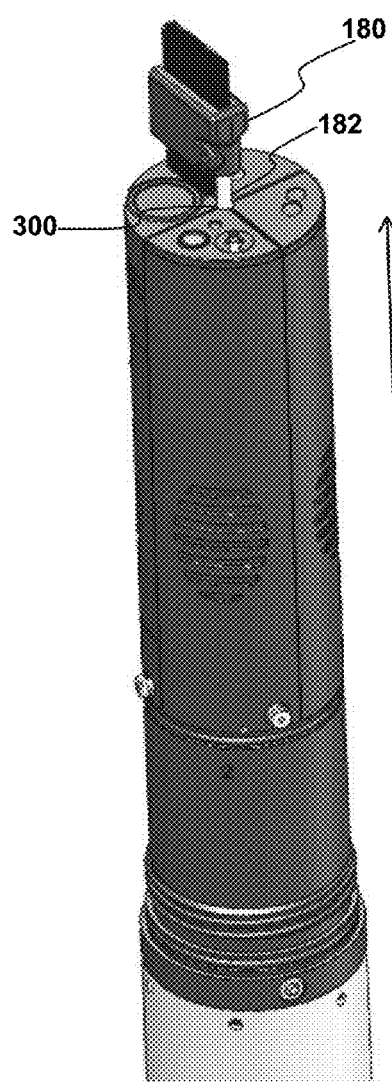
FIG. 8 is a three-dimensional rendering of the multi-parameter sonde with the sensor guard removed.

FIG. 7A-7D are views of a wiper 180 detached from the sonde, more specifically from a drive shaft of the sonde. The wiper may have a central body 183 with a lower surface 184 (FIG. 7C) and an upper surface 185 (FIG. 7A). A first wiper 186 and a second wiper 187 may connect to opposite surfaces for cleaning a distal sensing surface and an inward-facing surface of the sonde. In an aspect, the wipers may be brushes. The brushes may be configured to provide maximum cleaning area, with the brushes that clean the distal sensing surface cleaning a smaller overall area due to the presence of a drive shaft 182 terminating in a distal end 181 that is receivably positioned in a receiving passage 191 on the wiper 180.

Figure 12:
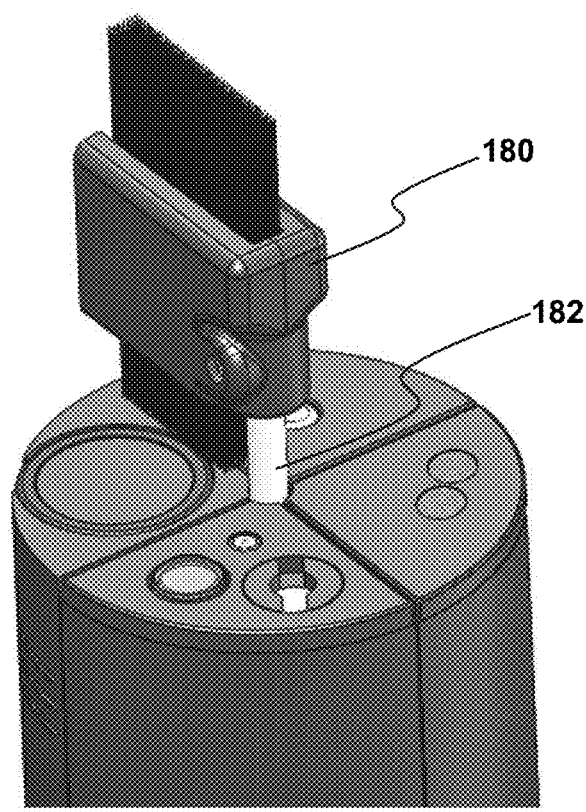
FIG. 12 is a close-up view of the continuous distal surface of the multi-parameter sonde of FIG. 8 with a wiper.
Figure 13:
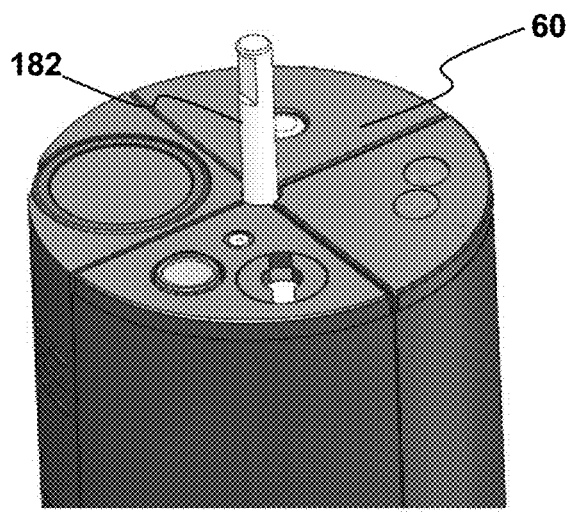
FIG. 13 shows the continuous distal surface of the multi-parameter sonde of FIG. 12 with the replaceable wiper removed, to better illustrate that the tight-fit between adjacent sensors leaves no observable spaces between the sensors, thereby improving wiping action with the wiper of FIG. 12.
Figure 16:
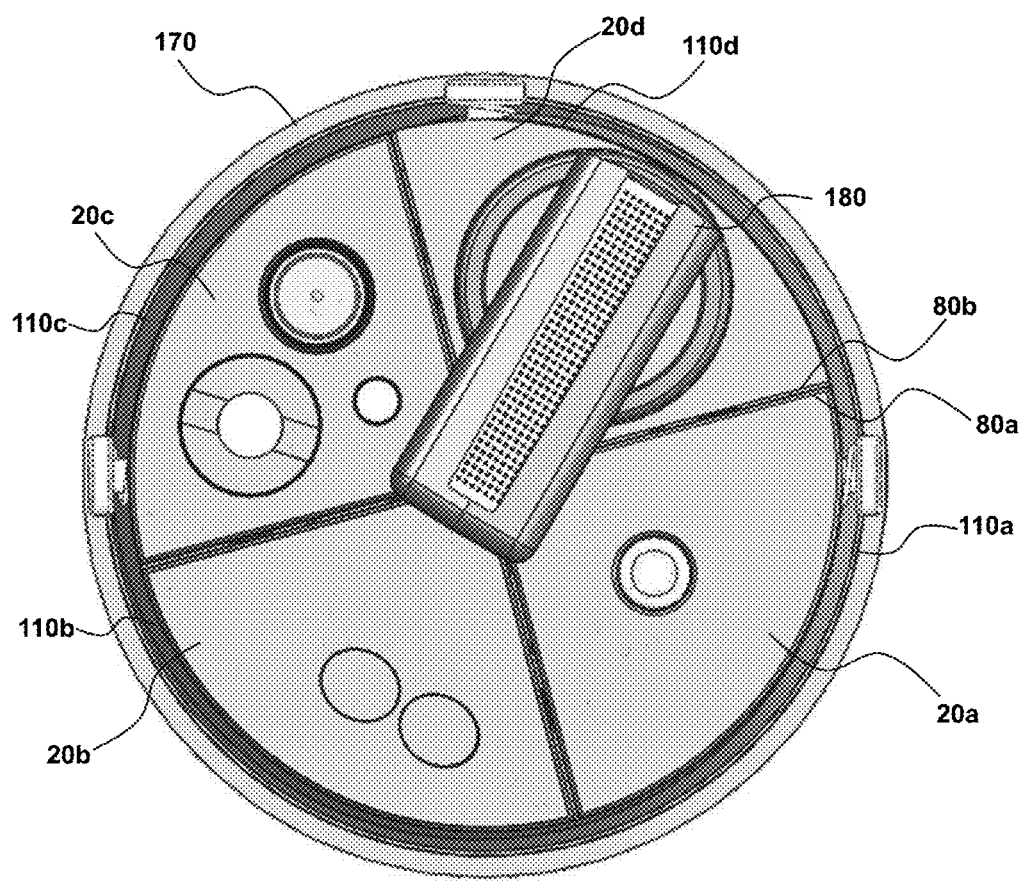
FIG. 16 longitudinally-directed view from the distal sensing surface toward the sonde base illustrating a cross-section outer surface of the plurality of sensors that is circular.

FIGS. 12-13 are a close-up view of the wiper installed configuration and a wiper removed configuration. FIG. 16 shows an end-on view of the wiper 180 and distal surfaces of a four-sensor embodiment, illustrated as sensors 20a 20b 20c 20d. Also illustrated is the tight fit between the sensor guard 170 and sensor outer facing surfaces 110a 110b 110c 110d. Side surfaces of adjacent surfaces are also in a tight-fit configuration, as called out by surfaces 80a 80b. In addition, the sonde has the capability to move the wiper brush 180° from the sensor it is currently reading. The sonde electronically detects the location of each probe installed from a unique resistor installed in the sensor. For sensors that are sensitive to the wiper brush's proximity, the brush moves to the opposite side during its measurement.

Figure 17:
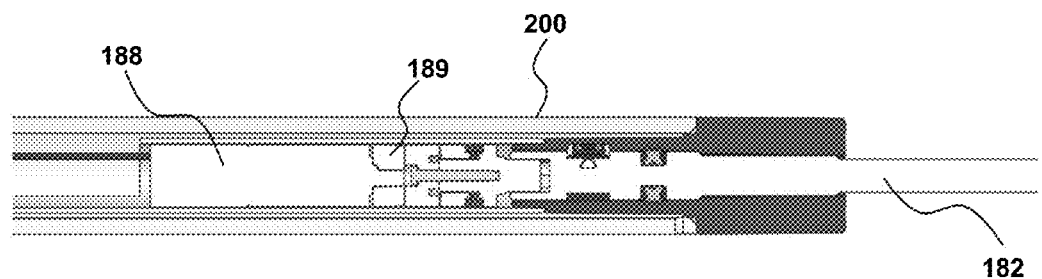
FIG. 17. Internal view of central support section containing motor and related components for turning a drive shaft to which a wiper is connected.

FIG. 17 is a schematic illustration of the various components and related geometry associated with turning a drive shaft to turn the wiper, including a motor 188, slip-clutch 189 and drive shaft 182. The parts required to move the drive shaft may be positioned within a central support, to which the plurality of sensors is connected. The slip-clutch is an important component that provides a number of functional benefits. For example, during sonde sensor handling and replacement, the brush is typically moved and without such a slip-clutch is vulnerable to breakage with attendant costly repair. The slip-clutch, accordingly, provides improved sonde sensor maintenance and repair, with a user simply moving the brush in any direction to facilitate access to the desired sensor.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every combination of elements described or exemplified herein can be used to practice the invention, unless otherwise stated.

Whenever a range is given in the specification, for example, a size range, an angle range, or a time or a number range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A multi-parameter sonde comprising:
   a plurality of independent sensors each having a distal sensing surface and a proximal end; and
   a base that operably connects to the proximal end of each of the sensors;
   wherein adjacent distal sensing surfaces substantially contact each other to form a continuous distal sensing surface comprising the plurality of independent sensors;
   wherein each of the plurality of independent sensors comprise:
      an inner corner edge;
      a pair of side surfaces extending from the inner corner edge and ending at an outer edge, wherein the side surfaces each define a plane and the planes are separated from each other by a side angle; and
      an outer facing surface that connects the pair of side surfaces at the outer edge, thereby forming a three-sided sensor housing;
   wherein when in use the side surfaces of adjacent sensors are in substantially continuous contact.

2. The multi-parameter sonde of claim 1, wherein the plurality of sensors form an outer surface having a circular cross-section.

3. The multi-parameter sonde of claim 1, wherein the base operably connects between 2 and 12 sensors and the side angle is independently selected from a range that is greater than or equal to 30° and less than 180°.

4. The multi-parameter sonde of claim 3, wherein the base operably connects four sensors, each sensor having a side angle of 90° and an outer facing surface with a curvature corresponding to one-quarter of a circle so that the plurality of sensors form an outer surface with a cross-section that is substantially circular.

5. The multi-parameter sonde of claim 4, wherein at least one of the sensors comprises a sensor blank having an external shape that corresponds to an external shape of one of the sensors.

6. The multi-parameter sonde of claim 1, further comprising a sensor-guard having a sensor receiving volume and a sample sensing volume, wherein the plurality of sensors occupy substantially the entire volume of the sensor receiving volume.

7. The multi-parameter sonde of claim 1, further comprising a central support extending from the base that independently releasably connects each of the plurality of sensors.

8. The multi-parameter sonde of claim 7, wherein each of the plurality of sensors comprises:
   a corner edge extending from the distal sensing surface and partway toward the proximal end, the corner edge shaped to receive at least a portion of the central support or a drive shaft extending therefrom;
   a pair of side surfaces that extend from the corner edge and that are separated from each other by a side angle; and
   an outer facing surface that connects the pair of side surfaces at an outer edge of each of the side surfaces, thereby forming a three-sided sensor housing.

9. The multi-parameter sonde of claim 8, wherein each of the plurality of sensors further comprise:
   a top portion of each of the pair of side surfaces having a top width;
   a bottom portion of each of the pair of side surfaces having a bottom width, wherein the bottom width is less than the top width to thereby form a bottom notch and a notch end surface;
   a tongue connected to the notch end surface and longitudinally extending partway down the notch;
   a fastening member to fasten the sensor to the base;
   wherein in combination, the plurality of sensors form:
      a top sensing volume having a central orifice for receiving a drive-shaft extending from the central support; and
      a bottom portion having a central receiving volume for receiving the central support and a drive shaft motor positioned therein; the central support having a plurality of grooves to operably receive the tongues and independently secure each of the sensors to the central portion.

10. The multi-parameter sonde of claim 9, wherein each of the plurality of sensors are tightly held against the central shaft, and a sensor guard is tight-fitted around an outer edge formed by the outer-facing surfaces of the sensors.

11. The multi-parameter sonde of claim 10, wherein the outer-facing surface is curved so that the plurality of sensors in combination form a circular cross-section.

12. The multi-parameter sonde of claim 10, wherein the plurality of sensors form a continuous outer-facing surface that is in a tight fit with an inner-facing surface of the sensor guard.

13. The multi-parameter sonde of claim 10, wherein a sensor side wall is in continuous contact with an adjacent sensor side wall, and wherein each of the sensors:
   extend a longitudinal distance that is greater than or equal to 5 cm and less than or equal to 50 cm;
   have a radial dimension that is greater than or equal to 1 cm and less than or equal to 10 cm; and
   in combination have a void volume that is less than or equal to 75 mL, wherein the void volume comprises at least one dimension associated with a sensor that is sufficiently small that biological growth is substantially constrained.

14. The multi-parameter sonde of claim 9, further comprising a wiper connected to a distal end of the drive shaft for rotably brushing each of the distal sensing surfaces.

15. The multi-parameter sonde of claim 14, further comprising a sensor guard that connects to the base and surrounds the plurality of sensors in a tight-fit configuration, the sensor guard having a sample sensing volume formed by a distal portion of a sensor guard sidewall, a sensor guard top surface, and the plurality of distal sensing surfaces, wherein the wiper is positioned within the sample sensing volume; and wherein the wiper comprises:
a central wiper body connected to the drive shaft, the central wiper body having a lower surface that faces the distal sensing surfaces and an upper surface that faces the sensor guard top surface;
a first wiper connected to the lower surface for cleaning the plurality of sensing surfaces; and
a second wiper connected to the upper surface for cleaning an inward-facing surface of the sensor guard top surface, wherein the first and second wipers each comprise a brush.

16. The multi-parameter sonde of claim 15, further comprising a motor and a slip clutch operably positioned in the central support and connected to the drive shaft to provide rotational motion of the drive shaft and the wiper connected thereto.

17. The multi-parameter sonde of claim 16, further comprising a position sensor operably connected to the motor to ensure wiper storage at a wiper stored position that does not adversely affect a sensor function, wherein the wiper storage position is at a position that is 180° from a sensor that is actively measuring a parameter.

18. The multi-parameter sonde of claim 1, further comprising a sensor guard that surrounds the plurality of sensors and connects to the base, wherein the sensor guard has:
a sensing end comprising a fluid opening;
a covering end that is liquid tight;
a cap configured to connect to both the sensing end and the covering end;
wherein the sensor guard is reversibly connected to the base to provide:
a sensor guard configuration for the sensing end aligned with the distal sensing surfaces and the covering end connected to the base; and
a sensor storage configuration for the covering end aligned with the distal sensing surfaces and the sensing end connected to the base;
wherein the sensor guard is configured to reversibly change between the sensor guard configuration and the sensor storage configuration.

19. The multi-parameter sonde of claim 18, wherein the cap has an internal surface that opposably faces the continuous sensing distal sensing surface and is separated from the continuous sensing distal sensing surface by a sample distance that is greater than or equal to 1 cm and less than or equal to 10 cm, the multi-parameter sonde further comprising:
a rotatable brush that traverses the sample distance for simultaneous cleaning of the continuous sensing distal surface and the cap internal surface.

20. The multi-parameter sonde of claim 18, wherein during immersion in water, an air pocket forms between an outer surface of the plurality of independent sensors and an inner surface of the guard, wherein no observable biological growth occurs on any sensor or guard contact surface in contact with the air pocket, wherein each sensor has a wetted region that is confined to within 5% of a sensor longitudinal length from the distal sensing surface.

21. The multi-parameter sonde of claim 1, further comprising:
a reversible sensor guard comprising:
a sensing end comprising a fluid opening;
a covering end that is liquid tight;
a cap that connects to either of the sensing end or the covering end;
wherein the reversible sensor guard is reversibly connected to the base to provide:
a sensor guard configuration for the sensing end aligned with the distal sensing surfaces and the covering end connected to the base; and
a sensor storage configuration for the covering end aligned with the distal sensing surfaces and the sensing end connected to the base; and
wherein the sensor guard is configured to reversibly change between the sensor guard configuration and the sensor storage configuration.

22. The multi-parameter sonde of claim 1, wherein adjacent sensors are separated from each other by an average separation distance that is less than 0.3 mm.

23. A sensor configured for use in a multi-parameter sonde, the sensor comprising:
an inner corner edge comprising a corner groove;
a pair of side surfaces extending from the inner corner edge and ending at an outer edge, wherein the side surfaces each define a plane and the planes are separated from each other by a side angle that is greater than or equal to 30° and less than 180°;
an outer facing surface that connects the pair of side surfaces at the outer edge, thereby forming a three-sided sensor housing;
a distal sensing surface;
a proximal end, wherein the pair of side surfaces and the outer-facing surface longitudinally extend between the proximal and the distal sensing surface to form a sensor housing; and
a sensor disposed within the sensor housing and having an active sensing end positioned at the distal sensing surface.

24. The sensor of claim 23, further comprising
a top portion of each of the pair of sides having a top width;
a bottom portion of each of the pair of sides having a bottom width, wherein the bottom width is less than the top width to thereby form a bottom notch and a notch end surface between the top portion and the bottom portion;
a tongue connected to the notch end surface and longitudinally extending partway down the notch; and
a fastening member connected to the proximal end for operably connecting the sensor to a multi-parameter sonde.

25. A method of monitoring one or more water parameters, the method comprising the steps of:
immersing the multi-parameter sonde of claim 21 into water, wherein the multi-parameter sonde is in the sensor guard configuration and the multi-parameter sonde is positioned in a direction with the distal end furthest from a surface of the water;
forming an air-pocket between an outer-facing surface of the sensors and an inner-facing surface of the guard, wherein the air-pocket forms over 90% or greater of a longitudinal distance of the sensors extending from the base, and less than 10% of the longitudinal distance from the distal sensing end is wetted; and
wherein observable biological growth is prevented in the air pocket and is confined to a biological growth area corresponding to the wetted distal sensor end.

* * * * *